US011571574B2

(12) United States Patent
Famm et al.

(10) Patent No.: US 11,571,574 B2
(45) Date of Patent: Feb. 7, 2023

(54) TREATMENT OF DISEASES MEDIATED BY THYROID AND PARATHYROID HORMONES

(71) Applicants: Galvani Bioelectronics Limited, Brentford Middlesex (GB); Tokyo Metropolitan Institute of Gerontology, Tokyo (JP)

(72) Inventors: Hans Jakob Kristoffer Famm, Stevenage (GB); Harumi Hotta, Tokyo (JP); Arun Sridhar, Stevenage (GB)

(73) Assignees: GALVANI BIOELECTRONICS LIMITED, Middlesex (GB); TOKYO METROPOLITAN INSTITUTE OF GERONTOLOGY, Tokyo (JP)

( * ) Notice: Subject to any disclaimer, the term of this patent is extended or adjusted under 35 U.S.C. 154(b) by 471 days.

(21) Appl. No.: 16/348,924

(22) PCT Filed: Nov. 10, 2017

(86) PCT No.: PCT/EP2017/078954
§ 371 (c)(1),
(2) Date: May 10, 2019

(87) PCT Pub. No.: WO2018/087330
PCT Pub. Date: May 17, 2018

(65) Prior Publication Data
US 2019/0262613 A1 Aug. 29, 2019

(30) Foreign Application Priority Data

Nov. 11, 2016 (GB) ...................................... 1619049

(51) Int. Cl.
*A61N 1/36* (2006.01)
*A61N 1/05* (2006.01)
(Continued)

(52) U.S. Cl.
CPC ....... *A61N 1/36121* (2013.01); *A61N 1/0556* (2013.01); *A61N 1/3606* (2013.01);
(Continued)

(58) Field of Classification Search
CPC .......................... A61N 1/36121; A61N 1/0556
(Continued)

(56) References Cited

U.S. PATENT DOCUMENTS 8,244,361 B1    8/2012  De Ridder
2003/0220669 A1*  11/2003  Shealy .................. A61N 1/327
                                                        607/2
(Continued)

FOREIGN PATENT DOCUMENTS

WO   WO 2004/098698 A2   11/2004
WO      2017/033101 A1    3/2017
(Continued)

OTHER PUBLICATIONS

International Search Report and Written Opinion dated Mar. 1, 2018 issued in PCT/EP2017/078954.

*Primary Examiner* — Nicole F Lavert
(74) *Attorney, Agent, or Firm* — Scully, Scott, Murphy & Presser, P.C.

(57) ABSTRACT

Modulation of neural activity in the superior laryngeal nerve (SLN) or cervical sympathetic trunk (CST) is effective in treating diseases and conditions mediated by thyroid and parathyroid hormones, in particular diseases associated with calcitonin secretion (e.g. osteoporosis) or diseases associated with thyroxine secretion (e.g. hypothyroid syndrome).

21 Claims, 13 Drawing Sheets

(51) Int. Cl.
*A61N 5/06* (2006.01)
*A61N 7/02* (2006.01)

(52) U.S. Cl.
CPC ..... *A61N 1/36053* (2013.01); *A61N 1/36157* (2013.01); *A61N 1/36175* (2013.01); *A61N 5/06* (2013.01); *A61N 7/022* (2013.01); *A61N 2005/0643* (2013.01)

(58) Field of Classification Search
USPC .......................................................... 607/68
See application file for complete search history.

(56) References Cited

U.S. PATENT DOCUMENTS

| | | | |
|---|---|---|---|
| 2007/0027483 A1 | 2/2007 | Maschino et al. | |
| 2015/0105840 A1* | 4/2015 | Boggs, II | A61N 1/0558 607/46 |
| 2015/0224307 A1* | 8/2015 | Bolea | A61N 1/3601 607/42 |
| 2016/0339239 A1* | 11/2016 | Yoo | A61N 1/36017 |

FOREIGN PATENT DOCUMENTS

| | | | | |
|---|---|---|---|---|
| WO | WO 2017/149437 A1 | | 9/2017 | |
| WO | WO 2017149437 | * | 9/2017 | ........... A61N 1/3606 |

* cited by examiner

FIG. 2C
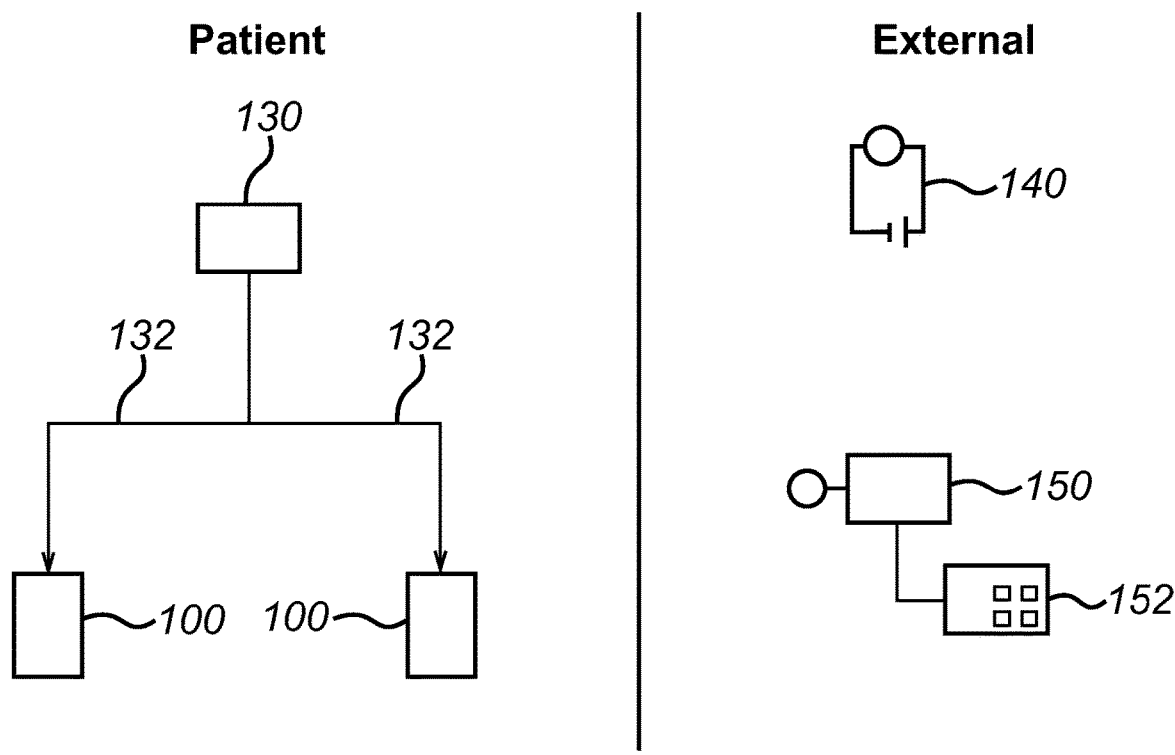
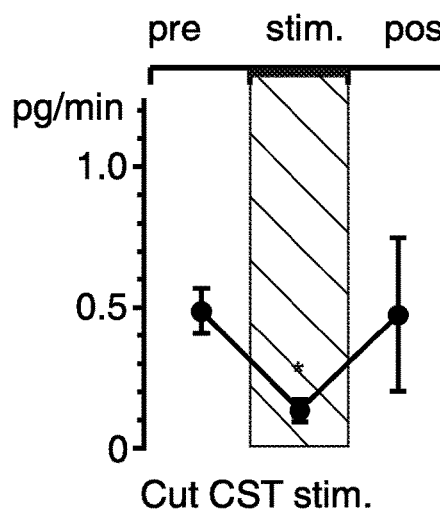
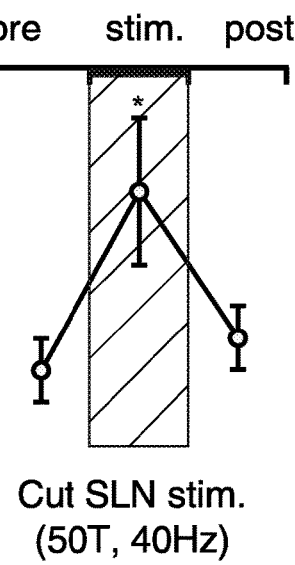
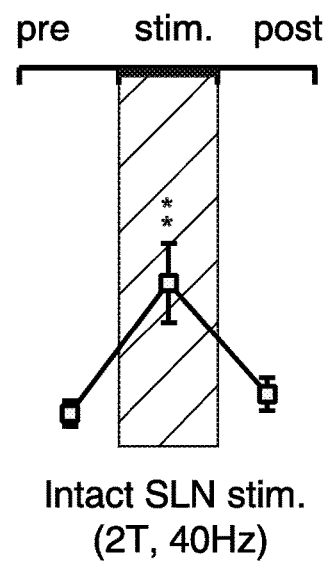
FIG. 3A — Cut CST stim. (50T, 5Hz)
FIG. 3B — Cut SLN stim. (50T, 40Hz)
FIG. 3C — Intact SLN stim. (2T, 40Hz)

FIG. 4A Cut CST stim. (50T)
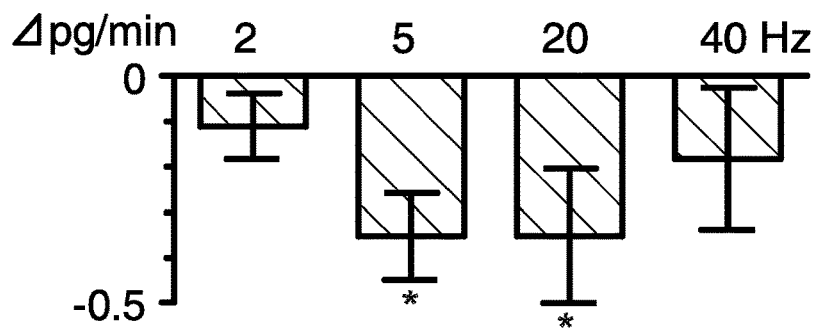
FIG. 4B Cut SLN stim. (50T)
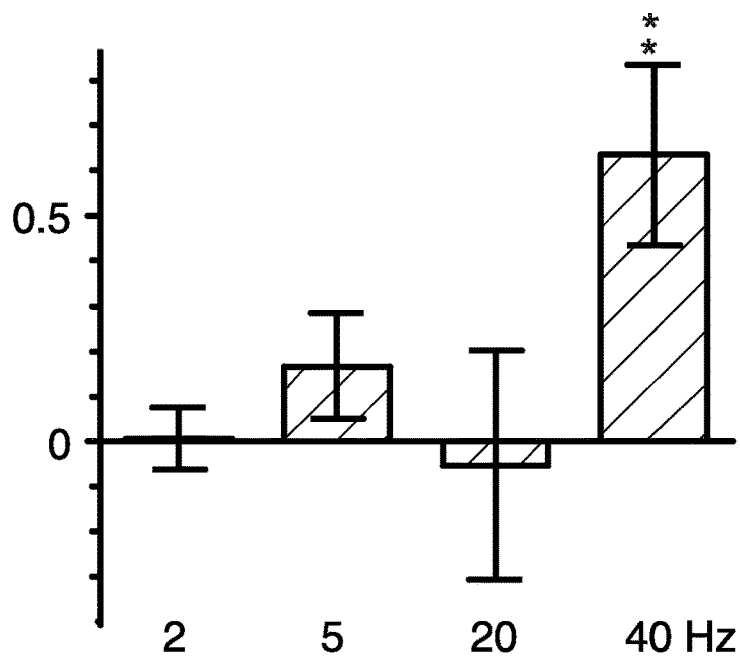
FIG. 4C Intact SLN stim. (2T)
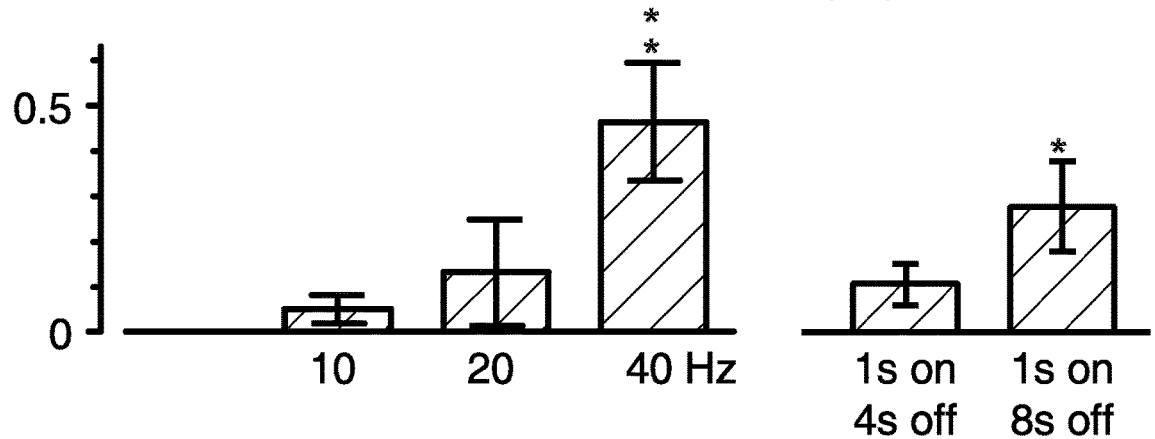

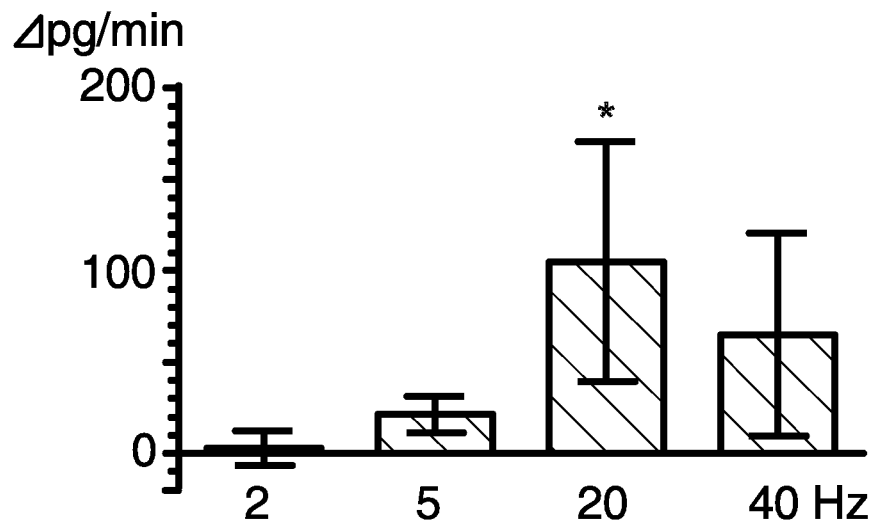
FIG. 5A Cut CST stim. (50T)
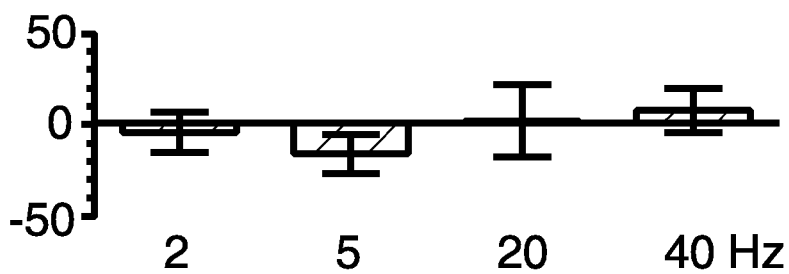
FIG. 5B Cut SLN stim. (50T)
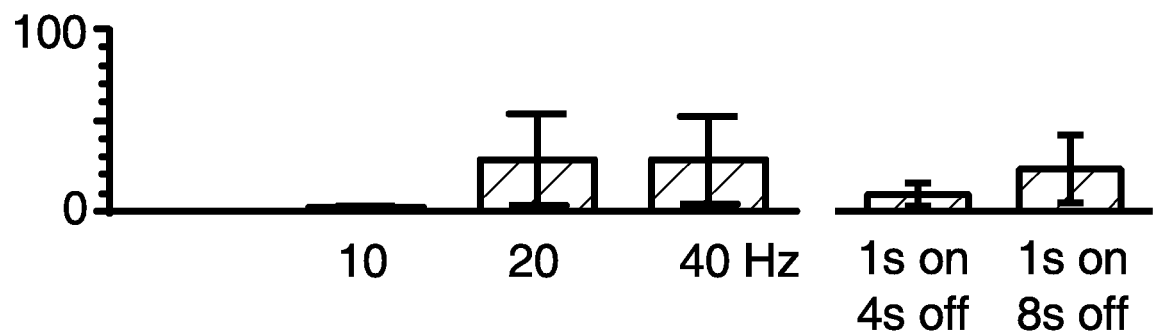
FIG. 5C Intact SLN stim. (2T)

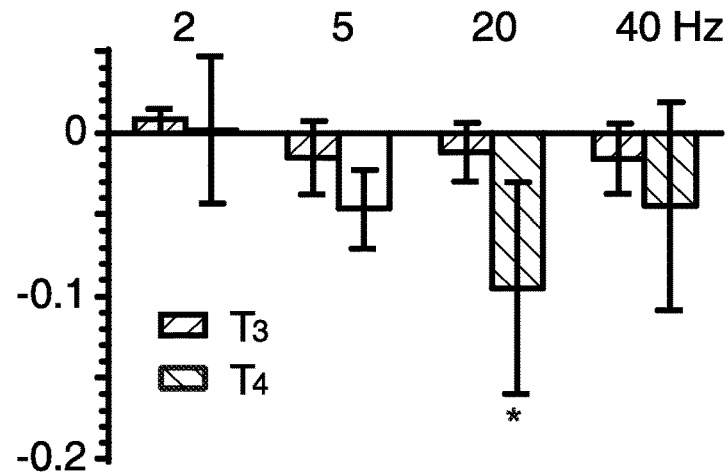
FIG. 6A Cut CST stim. (50T)
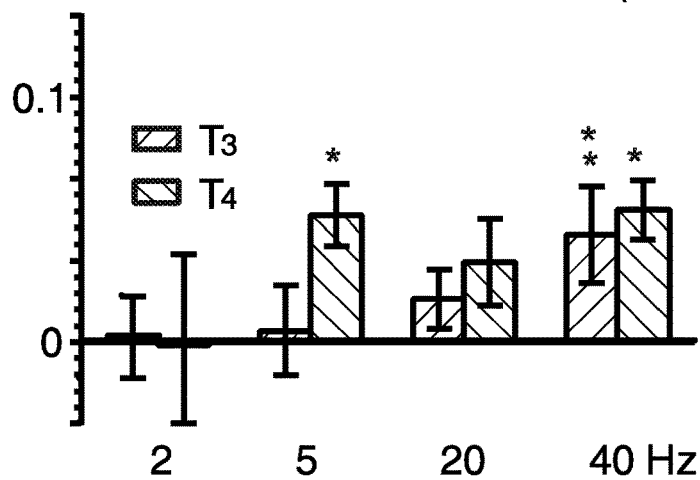
FIG. 6B Cut SLN stim. (50T)
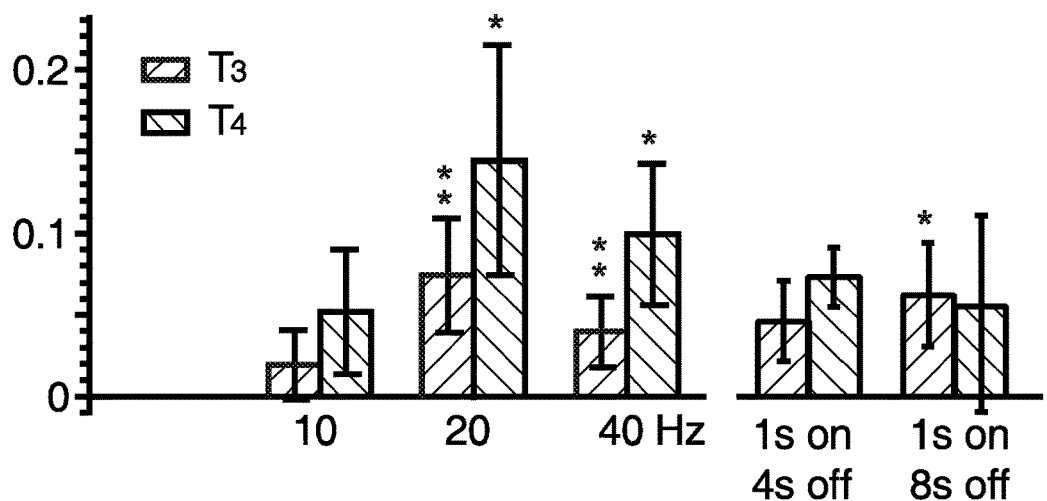
FIG. 6C Intact SLN stim. (2T)

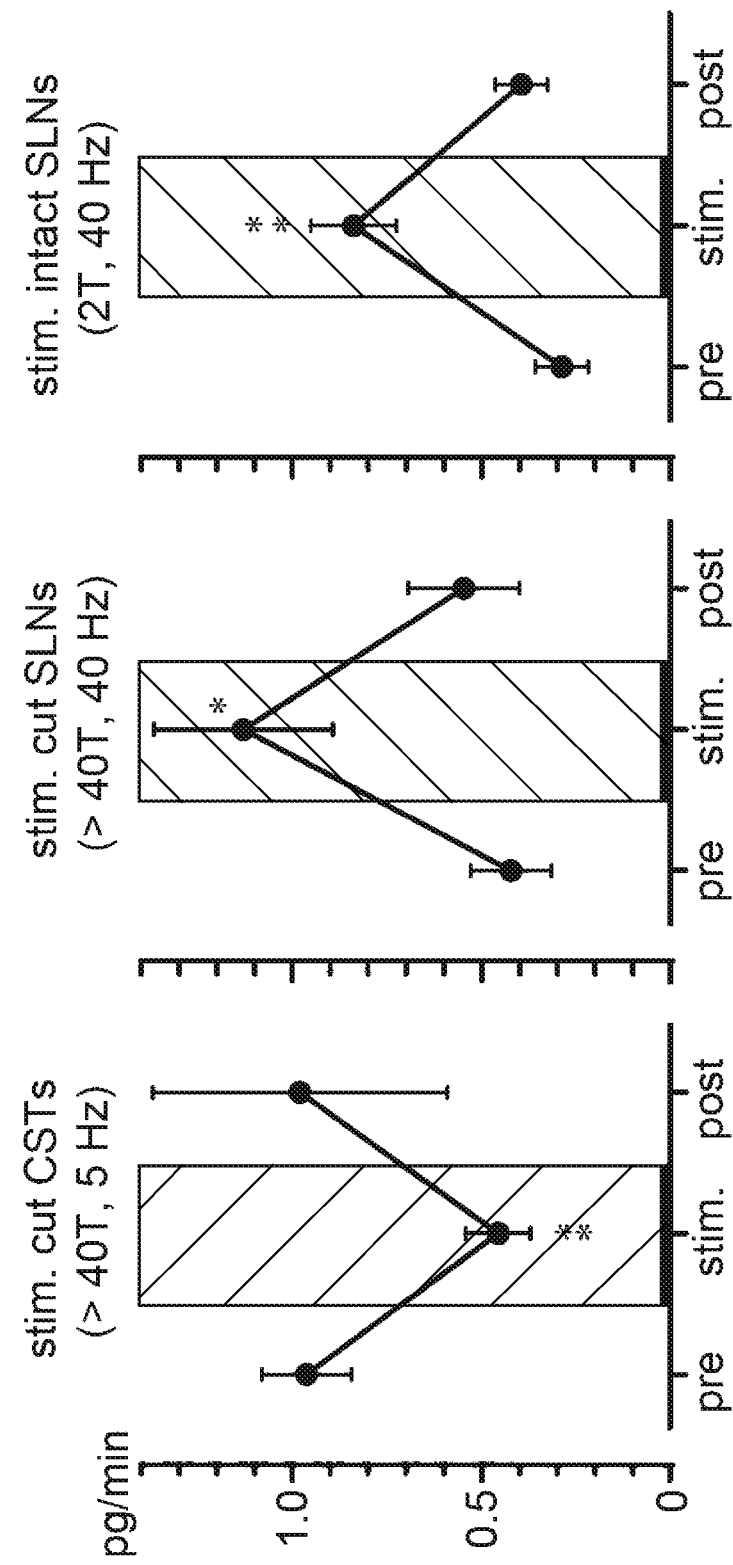

stim. cut CSTs (> 40T)

stim. cut SLNs (> 40T)

stim. intact SLNs (2T)

stim. cut CSTs (> 40T)

stim. cut SLNs (> 40T)

stim. intact SLNs (2T)

stim. cut CSTs (> 40T)

stim. cut SLNs (> 40T)

stim. intact SLNs (2T)

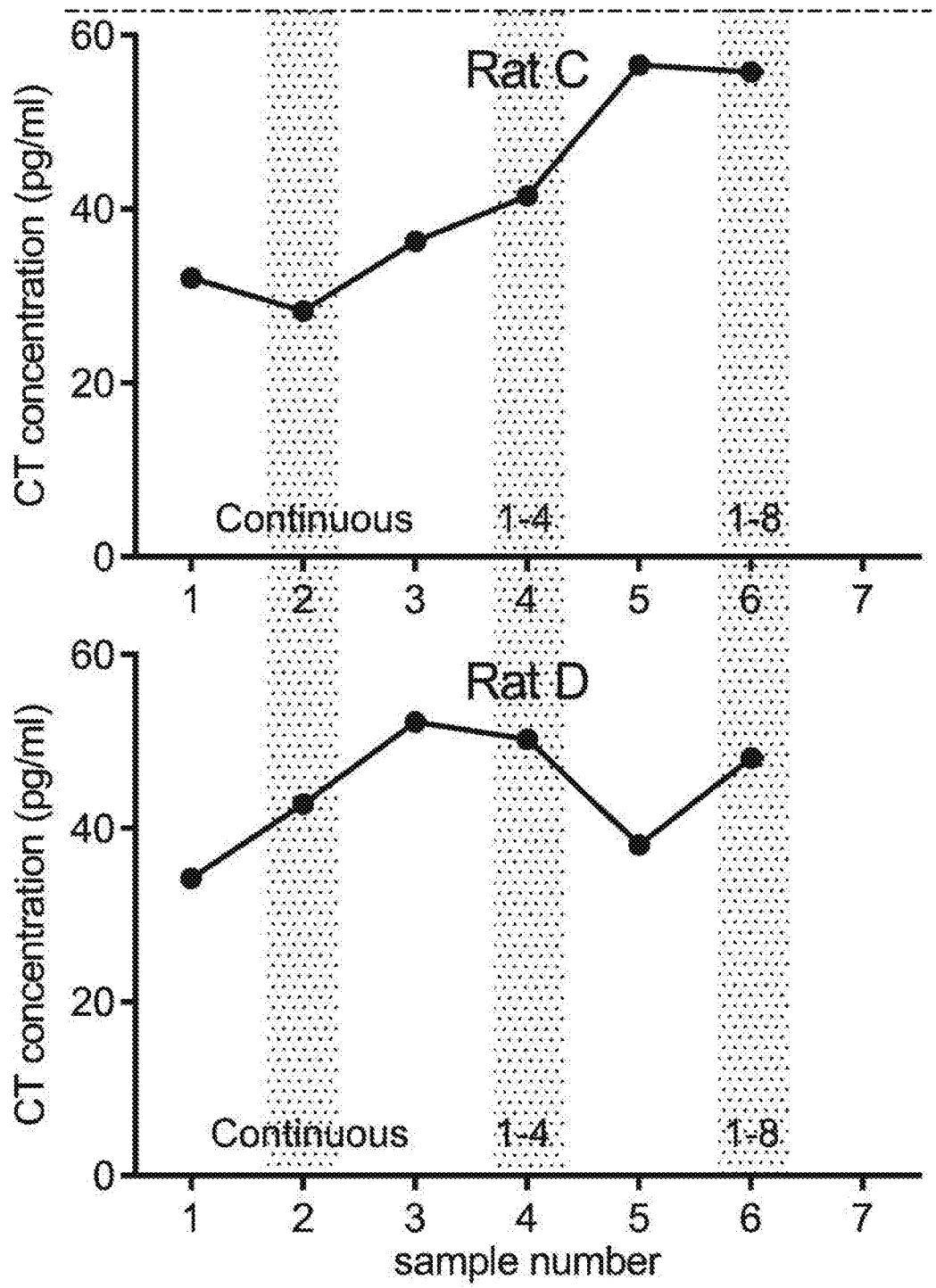
FIG. 11(contd.)

TREATMENT OF DISEASES MEDIATED BY THYROID AND PARATHYROID HORMONES

FIELD OF THE INVENTION

The present invention relates to methods and devices for treatment of diseases mediated by thyroid and parathyroid hormones, in particular by stimulation of neural activity in the superior laryngeal nerve (SLN) or cervical sympathetic trunk (CST).

BACKGROUND OF THE INVENTION

Thyroid and parathyroid glands receive dual innervation by sympathetic nerves (cervical sympathetic trunk: CST) and parasympathetic nerves (superior laryngeal nerve: SLN). Blood flow of the glands is reciprocally regulated by this dual innervation. Hormones secreted from the glands are known to be regulated by hormonal factors, and the possibility of neuronal regulation by the autonomic nerves has been suggested by pharmacological and denervation experiments.

Hormones secreted by the thyroid and parathyroid glands, for example calcitonin (CT), thyroxine (T4) and its metabolite triiodothyronine (T3), and parathyroid hormone (PTH), act to homeostatically regulate factors such as the body's calcium and phosphate levels, for example by fixing or releasing calcium from bone through osteoblast or osteoclast activity. Disruption of thyroid and parathyroid hormone levels has been reported in bone conditions such as osteoporosis, osteoarthritis, Paget's disease of bone, Hashimoto's disease, as well as mental health disorders such as depression, anxiety, bipolar disorder and mania.

Pharmacological treatment of these disorders can include hormone replacement, for example administration of salmon calcitonin. Other approaches include targeting the pathophysiological mechanisms, for example using osteoclast inhibitors such as bisphosphonates in osteoporosis therapy. However, these therapies have disadvantages such as poor pharmacokinetic properties (e.g. the short half-life of salmon calcitonin) or frequent occurrence of side-effects (e.g. bisphosphonates).

There is therefore an unmet need for interventions able to treat disorders and diseases associated with thyroid and parathyroid hormone disruption.

SUMMARY OF THE INVENTION

The apparatuses and methods provided herein address the problem of treating disease mediated by thyroid and parathyroid hormones such as calcitonin, thyroxine and parathyroid hormone (PTH). In particular, the apparatuses and methods provided herein address the problem using electrical devices stimulating neural activity in the superior laryngeal nerve (SLN) or in the cervical sympathetic trunk (CST). These apparatuses and methods have the advantage of ameliorating the symptoms of the conditions but without the problems associated with current therapies, such as the short half-life of calcitonin therapy. Moreover, selective stimulation of the neural activity in the myelinated fibres of the SLN, preferably the large myelinated fibres of the SLN, is particularly advantageous because it permits effective treatment at lower (and therefore less damaging and less power demanding) signal intensity, and also avoids possible unwanted downstream side-effects arising from stimulation of small unmyelinated fibres (c-fibres).

Therefore, in a first aspect is provided an apparatus for stimulating the neural activity of at least one superior laryngeal nerve (SLN) of a patient, the apparatus comprising: an actuator configured to apply a signal to said at least one SLN of the patient; and a controller coupled to the actuator, the controller controlling the signal to be applied by the actuator, such that the signal stimulates the neural activity of the SLN to produce a physiological response in the patient. In certain embodiments the physiological response is one or more of: an increase in circulating calcitonin, an increase in bone density, a decrease in bone resorption and/or an increase in bone formation.

Also provided is an apparatus for stimulating the neural activity of at least one cervical sympathetic trunk (CST) of a patient, the apparatus comprising: an actuator configured to apply a signal to said at least one CST of the patient; and a controller coupled to the actuator, the controller controlling the signal to be applied by the actuator, such that the signal stimulates the neural activity of the CST to produce a physiological response in the patient. In certain embodiments the physiological response is one or more of: a decrease in circulating calcitonin, a decrease in circulating T4, an increase in circulating PTH, a decrease in bone density, an increase in bone resorption and/or a decrease in bone formation.

In a second aspect is provided a method of treating a calcitonin-associated disease, optionally osteoporosis, in a patient comprising: implanting in the patient an apparatus for stimulating the neural activity of at least one superior laryngeal nerve (SLN) of a patient according to the invention; positioning the actuator of the apparatus in signaling contact with a SLN of the patient; activating the apparatus.

Also provided is a method of treating a thyroxine-associated disease, optionally hypothyroid syndrome, in a patient comprising: implanting in the patient an apparatus for stimulating the neural activity of at least one cervical sympathetic trunk (CST) of a patient according to the invention; positioning the actuator of the apparatus in signaling contact with a CST of the patient; activating the apparatus.

In a third aspect is provided a method of treating a calcitonin-associated disease in a patient, the method comprising applying a signal to a part or all of a SLN of said patient to stimulate neural activity in said nerve in the patient. In certain embodiments, the signal is applied by a neuromodulation apparatus comprising at least one actuator configured to apply the signal.

Also provided is a method of treating a thyroxine-associated disease in a patient, the method comprising applying a signal to a part or all of a CST of said patient to stimulate the neural activity of said nerve in the patient. In certain embodiments, the signal is applied by a neuromodulation apparatus comprising at least one actuator configured to apply the signal.

In a fourth aspect is provided a neuromodulatory electrical waveform for use in a method of treating a calcitonin-associated disease in a patient, wherein the method comprises applying the waveform to a SLN of the patient, and wherein the waveform has a frequency of 10-50 Hz and intensity of 0.5 T-5.0 T, such that, when applied to a SLN of the patient, the waveform increases neural signaling in the SLN to which the signal is applied, preferably increases neural activity in the myelinated fibres of the SLN to which it is applied, preferably selectively increases neural activity in the myelinated fibres of the SLN to which it is applied, preferably selectively increases neural activity in the large myelinated fibres of the SLN to which it is applied.

In a fifth aspect is provided the use of a neuromodulation apparatus for treating a calcitonin-associated disease in a patient by increasing neural activity in a SLN of the patient, preferably increasing neural activity in the myelinated fibres of the SLN, preferably selectively increasing neural activity in the myelinated fibres of the SLN, preferably selectively increasing neural activity in the large myelinated fibres of the SLN.

In a sixth aspect is provided a pharmaceutical composition for use in a method of treating a calcitonin-associated disease in a subject, wherein the composition comprises a compound for treating a calcitonin-associated disease, and wherein the method is a method according to the second or third aspect, the method further comprising the step of administering an effective amount of the pharmaceutical composition to the subject.

In a seventh aspect is provided a pharmaceutical composition comprising a compound for treating a calcitonin-associated disease, for use in treating a calcitonin-associated disease in a subject, the subject having an apparatus according to the first aspect.

In an eighth aspect is provided a neuromodulation system comprising a plurality of apparatuses according to the first aspect.

In a further aspect provided herein is a modified superior laryngeal nerve (SLN), wherein the nerve membrane is reversibly depolarized by an electric field, such that an action potential is generated de novo in the modified nerve.

In a further aspect provided herein is a modified cervical sympathetic trunk (CST) nerve, wherein the nerve membrane is reversibly depolarized by an electric field, such that an action potential is generated de novo in the modified nerve.

The invention also provides a modified superior laryngeal nerve (SLN) to which one or more actuator of the system or device of the invention is attached, wherein the one or more actuator is in signaling contact with the nerve and so the nerve can be distinguished from the nerve in its natural state, and wherein the nerve is located in a subject who suffers from or is at risk of developing a calcitonin-associated disease.

The invention also provides a modified cervical sympathetic trunk (CST) nerve to which one or more actuator of the system or device of the invention is attached, wherein the one or more actuator is in signaling contact with the nerve and so the nerve can be distinguished from the nerve in its natural state, and wherein the nerve is located in a subject who suffers from or is at risk of developing a thyroxine-associated disease.

The invention also provides an SLN nerve obtainable by modulating neural activity of the SLN nerve, respectively, according to a method of the invention.

The invention also provides a CST nerve obtainable by modulating neural activity of the CST nerve, respectively, according to a method of the invention.

The invention also provides a nerve selected from a cervical sympathetic trunk (CST) nerve or a superior laryngeal nerve (SLN), wherein the nerve is bounded by a nerve membrane, comprising a distribution of potassium and sodium ions movable across the nerve membrane to alter the electrical membrane potential of the nerve so as to propagate an action potential along the nerve in a normal state; wherein at least a portion of the nerve is subject to the application of a temporary external electrical field which modifies the concentration of potassium and sodium ions within the nerve, causing depolarization of the nerve membrane, thereby, in a disrupted state, temporarily generating an action potential de novo across that portion; wherein the nerve returns to its normal state once the external electrical field is removed.

In a further aspect provided herein is a charged particle for use in a method of treating or preventing a calcitonin-associated disease, wherein the charged particle causes reversible depolarization of the nerve membrane of a superior laryngeal nerve (SLN), such that an action potential is generated de novo in the modified SLN.

Further provided is a charged particle for use in a method of treating or preventing a thyroxine-associated disease, wherein the charged particle causes reversible depolarization of the nerve membrane of a cervical sympathetic trunk (CST) nerve, such that an action potential is generated de novo in the modified CST.

BRIEF DESCRIPTION OF THE FIGURES

FIG. 3: iCT secretion rate before (pre), during (stim) and following (post) stimulation with indicated parameters of (A) cut CSTs, (B) cut SLNs, (C) intact SLNs.

FIG. 4: iCT secretion rate during stimulation with the indicated parameters of (A) cut CSTs, (B) cut SLNs, (C) intact SLNs.

FIG. 5: iPTH secretion rate during stimulation with the indicated parameters of (A) cut CSTs, (B) cut SLNs, (C) intact SLNs.

FIG. 6: iT3 (left paired bar) and iT4 (right paired bar) secretion rates during stimulation with the indicated parameters of (A) cut CSTs, (B) cut SLNs, (C) intact SLNs.

FIG. 7: iCT secretion rate before (pre), during (stim) and following (post) stimulation with indicated parameters of: (A) cut CSTs, (B) cut SLNs, (C) intact SLNs. *p<0.05, **p<0.01 (significant differences were determined by comparison with the prestimulus values).

DETAILED DESCRIPTION

Figure 1:
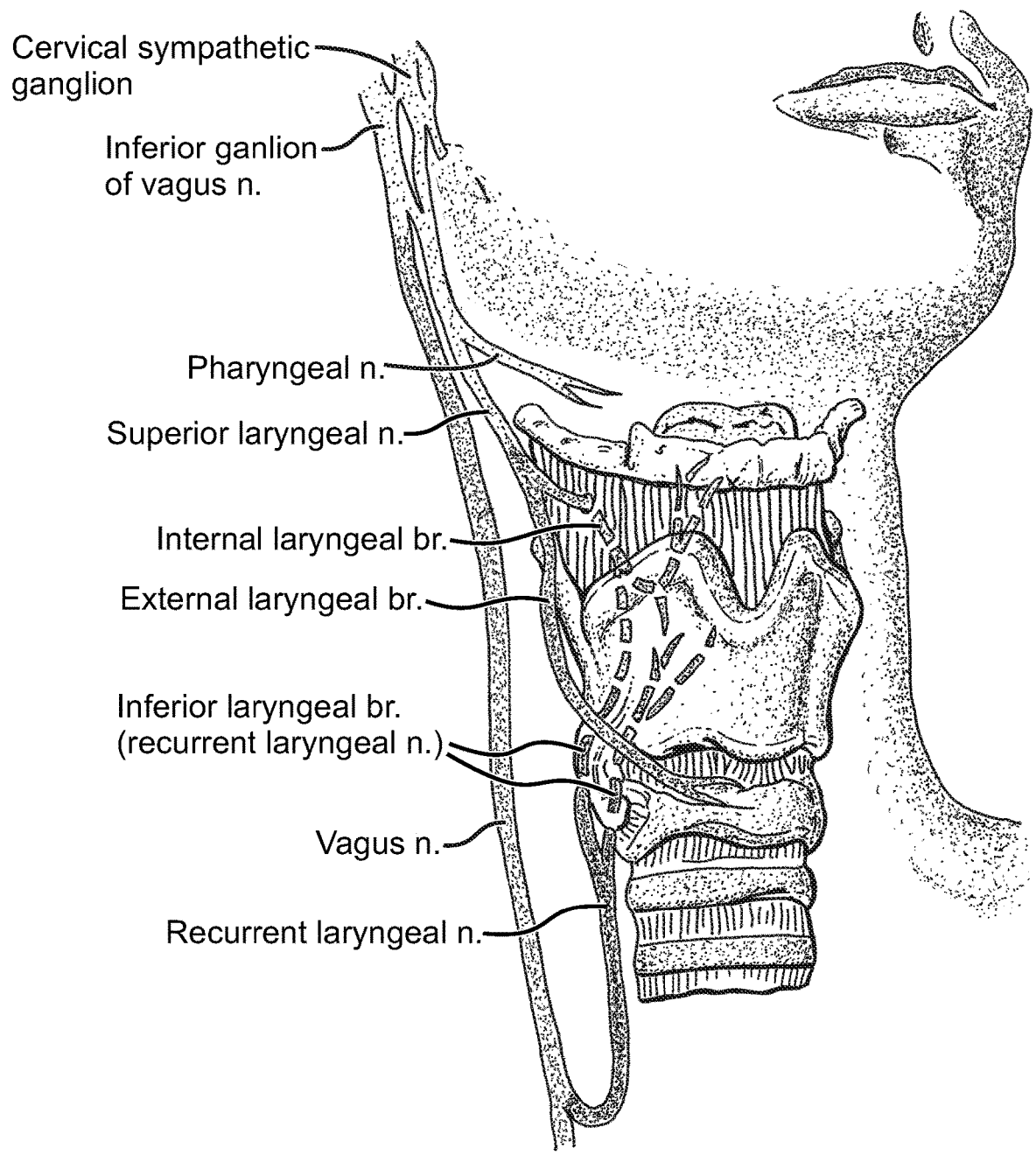
FIG. 1: Schematic drawing showing innervation of the right hand side of the human neck. Cervical sympathetic ganglion is also referred to herein as cervical sympathetic trunk (CST). "Superior laryngeal n." is the superior laryngeal nerve (SLN). Taken from "Atlas of Regional Anesthesia, 3rd ed.".

The terms as used herein are given their conventional definition in the art as understood by the skilled person, unless otherwise defined below. In the case of any inconsistency or doubt, the definition as provided herein should take precedence.

As used herein, application of a signal may equate to the transfer of energy in a suitable form to carry out the intended effect of the signal. That is, application of a signal to a nerve or nerves may equate to the transfer of energy to (or from) the nerve(s) to carry out the intended effect. For example, the energy transferred may be electrical, mechanical (including acoustic, such as ultrasound), electromagnetic (e.g. optical), magnetic or thermal energy. It is noted that application of a signal as used herein does not include a pharmaceutical intervention.

As used herein, "actuator" is taken to mean any element of applying a signal to the intended nerve, for example an electrode, diode, Peltier element or ultrasound actuator.

As used herein, "neural activity" of a nerve is taken to mean the signaling activity of the nerve, for example the amplitude, frequency and/or pattern of action potentials in the nerve.

Modulation of neural activity, as used herein, is taken to mean that the signaling activity of the nerve is altered from the baseline neural activity—that is, the signaling activity of the nerve in the patient prior to any intervention. Such modulation may increase, inhibit, block, or otherwise change the neural activity compared to baseline activity.

Stimulation of neural activity is taken to mean an increase of neural activity, for example an increase in the total signaling activity of the whole nerve, or that the total signaling activity of a subset of nerve fibres of the nerve is increased, compared to baseline neural activity in that part of the nerve.

The increase may be an increase in the signaling activity of the myelinated fibres of the nerve. As used herein, a selective increase in the signaling activity of the myelinated fibres of the nerve is taken to mean that there is a preferential increase in neural activity of the myelinated fibres of the nerve compared to in the unmyelinated fibres. Preferably, selective stimulation of the myelinated fibres of a subject nerve does not lead to an increase in neural signaling in the unmyelinated nerve fibres of the subject nerve. As used herein, a selective increase in the signaling activity of the large myelinated fibres of the nerve is taken to mean that there is a preferential increase in neural activity of the large myelinated fibres of the nerve compared to in the small myelinated fibres and unmyelinated fibres. Preferably, selective stimulation of the large myelinated fibres of a subject nerve does not lead to an increase in neural signaling in the small myelinated fibres and unmyelinated fibres of the subject nerve. In this context, "large myelinated fibres" are also known in the art as "A fibres", "small myelinated fibres" are also known in the art as "B fibres", and unmyelinated fibres are also known as "C fibres".

Where the modulation of neural activity is inhibition of neural activity, such inhibition may be partial inhibition. Partial inhibition may be such that the total signaling activity of the whole nerve is partially reduced, or that the total signaling activity of a subset of nerve fibres of the nerve is fully reduced (i.e. there is no neural activity in that subset of fibres of the nerve), or that the total signaling of a subset of nerve fibres of the nerve is partially reduced compared to baseline neural activity in that subset of fibres of the nerve. Where the modulation of neural activity is inhibition of neural activity, this also encompasses full inhibition of neural activity in the nerve—that is, there is no neural activity in the whole nerve.

Where inhibition of neural activity is a block on neural activity, such blocking may be a partial block—i.e. blocking of neural activity in a subset of nerve fibres of the nerve. Alternatively, such blocking may be a full block—i.e. blocking of neural activity in the whole nerve. A block on neural activity is understood to be blocking neural activity from continuing past the point of the block. That is, when the block is applied, action potentials may travel along the nerve or subset of nerve fibres to the point of the block, but not beyond the point of the block.

Modulation of neural activity may also be an alteration in the pattern of action potentials. It will be appreciated that the pattern of action potentials can be modulated without necessarily changing the overall frequency. For example, modulation of the neural activity may be such that the pattern of action potentials is altered to more closely resemble a healthy state rather than a disease state—i.e. to more closely resemble the pattern in a healthy individual.

Modulation of neural activity may comprise altering the neural activity in various other ways, for example increasing or inhibiting a particular part of the neural activity and/or stimulating new elements of activity, for example in particular intervals of time, in particular frequency bands, according to particular patterns and so forth. Such altering of neural activity may for example represent both increases and/or decreases with respect to the baseline activity.

Modulation (for example stimulation) of the neural activity may be temporary. As used herein, "temporary" is taken to mean that the modulated neural activity (for example stimulation) is not permanent. That is, the neural activity following cessation of the signal is substantially the same as the neural activity prior to the signal being applied—i.e. prior to modulation.

Modulation (for example stimulation) of the neural activity may be persistent. As used herein, "persistent" is taken to mean that the modulated neural activity (for example stimulation) has a prolonged effect. That is, upon cessation of the signal, neural activity in the nerve remains substantially the same as when the signal was being applied—i.e. the neural activity during and following modulation is substantially the same.

Modulation (for example stimulation) of the neural activity may be corrective. As used herein, "corrective" is taken to mean that the modulated neural activity (for example stimulation) alters the neural activity towards the pattern of neural activity in a healthy individual. That is, upon cessation of the signal, neural activity in the nerve more closely resembles the pattern of action potentials in the nerve observed in a healthy subject than prior to modulation, preferably substantially fully resembles the pattern of action potentials in the nerve observed in a healthy subject.

Such corrective modulation caused by the signal can be any modulation as defined herein.

For example, application of the signal may result in stimulation of neural activity, and upon cessation of the signal, the pattern of action potentials in the nerve resembles the pattern of action potentials observed in a healthy subject.

As used herein, a "healthy individual" or "healthy subject" is an individual not exhibiting the symptoms of a calcitonin-associated disease or a thyroxine-associated disease.

As used herein, a "calcitonin-associated disease" is taken to mean a disease associated with disrupted levels of calcitonin in the patient compared to the levels of a healthy individual. Calcitonin-associated diseases may also be characterized by increased levels of blood calcium, increased osteoclast activity, increased bone resorption, decreased osteoblast activity, decreased bone formation. "Calcitonin-associated disease" includes conditions such as osteoporosis, osteoarthritis, hyperthyroidism, Paget's disease of bone. "Calcitonin-associated disease" also includes conditions such as bipolar disorder, mania and depression.

As used herein, a "thyroxine-associated disease" is taken to mean a disease associated with disrupted levels of thyroxine (also known as T4) and/or its metabolite hormone triiodothyronine (also known as T3) in the patient compared to the levels of a healthy individual. Thyroxine-associated diseases may also be characterized by decreased levels of blood calcium, increased osteoclast activity, increased bone resorption, decreased osteoblast activity, decreased bone formation. "Thyroxine-associated disease" includes conditions such as hypothyroid syndrome, Hashimoto's disease, and obesity. "Thyroxine-associated disease" also includes conditions such as depression.

As used herein, an "improvement in a measurable physiological parameter" is taken to mean that for any given physiological parameter, an improvement is a change in the value of that parameter in the patient towards the normal value or normal range for that value—i.e. towards the expected value in a healthy individual.

For example, in a patient with a calcitonin-associated disease, an improvement in a measurable parameter may be: an increase in circulating calcitonin, a decrease in bone resorption (indicated by, for example, a decrease in N-telopeptide of type 1 collagen (NTX), C-terminal telopeptide of type 1 collagen (CTX), and/or pyridinoline cross-links), an increase in bone density, and/or an increase in bone formation (indicated by, for example, an increase in bone-specific alkaline phosphatase (BALP), osteocalcin, and/or N-terminal propeptide of type 1 procollagen (P1NP). By way of further example, in a patient with a thyroxine-associated disease, an improvement in a measurable parameter may be: a decrease in circulating calcitonin, a decrease in circulating T4, an increase in circulating PTH, an increase in bone resorption (indicated by, for example, an increase in N-telopeptide of type 1 collagen (NTX), C-terminal telopeptide of type 1 collagen (CTX), and/or pyridinoline cross-links), a decrease in bone density, and/or a decrease in bone formation (indicated by, for example, a decrease in bone-specific alkaline phosphatase (BALP), osteocalcin, and/or N-terminal propeptide of type 1 procollagen (P1NP).

As used herein, a physiological parameter is not affected by modulation of the neural activity if the parameter does not change as a result of the modulation from the average value of that parameter exhibited by the subject or patient when no intervention has been performed—i.e. it does not depart from the baseline value for that parameter.

The skilled person will appreciate that the baseline for any neural activity or physiological parameter in an individual need not be a fixed or specific value, but rather can fluctuate within a normal range or may be an average value with associated error and confidence intervals. Suitable methods for determining baseline values would be well known to the skilled person.

As used herein, a measurable physiological parameter is detected in a patient when the value for that parameter exhibited by the patient at the time of detection is determined. A detector is any element able to make such a determination.

A "predefined threshold value" for a physiological parameter is the value for that parameter where that value or beyond must be exhibited by a subject or patient before the intervention is applied. For any given parameter, the threshold value may be defined as a value indicative of a pathological state (e.g. the patient has abnormal levels of one or more hormones, or abnormal levels of circulating calcium) or of a particular physiological state. Examples of such predefined threshold values include parasympathetic or sympathetic tone (neural, hemodynamic (e.g. heart rate, blood pressure, heart rate variability) or circulating plasma biomarkers) greater than a threshold parasympathetic or sympathetic tone; abnormal bone formation or resorption compared to a healthy individual, abnormal SLN activity compared to a healthy individual (for instance a decrease in SLN neural activity), abnormal CST neural activity (for instance a decrease in CST neural activity), or abnormal vagal nerve activity. Such a threshold value for a given physiological parameter is exceeded if the value exhibited by the patient is beyond the threshold value—that is, the exhibited value is a greater departure from the normal or healthy value for that parameter than the predefined threshold value.

The measurable physiological parameter may comprise an action potential or pattern of action potentials in one or more nerves of the patient, wherein the action potential or pattern of action potentials is associated with a calcitonin-associated disease or a thyroxine-associated disease. Suitable nerves in which to detect an action potential or pattern of action potentials include a SLN, a CST nerve and/or a vagal nerve (for example a branch of a vagal nerve e.g. the right cervical cardiac branch). In a particular embodiment, the measurable physiological parameter comprises the pattern of action potentials in the SLN.

Treatment of a calcitonin-associated disease may be characterized by any one or more of an increase in circulating calcitonin, an increase in bone density, a decrease in bone resorption and/or an increase in bone formation, and/or a change in the pattern of action potentials or activity of the SLN nerve, CST nerve or vagal nerve towards that of a healthy individual.

Treatment of a thyroxine-associated disease may be characterized by any one or more of a decrease in circulating calcitonin, a decrease in circulating T4, an increase in circulating PTH, a decrease in bone density, an increase in bone resorption and/or a decrease in bone formation.

Treatment of a calcitonin-associated disease or a thyroxine-associated disease may be prophylactic or therapeutic.

A "neuromodulation apparatus" as used herein is an apparatus or device configured to modulate the neural activity of a nerve. "Device" and "apparatus" are used interchangeably herein. Neuromodulation apparatuses or devices as described herein comprise at least one actuator capable of effectively applying a signal to a nerve. In those embodiments in which the neuromodulation apparatus is at least partially implanted in the patient, the elements of the apparatus that are to be implanted in the patient are constructed such that they are suitable for such implantation. Such suitable constructions would be well known to the skilled person. Indeed, various fully implantable neuromodulation devices have been implanted into human patients, such as the INTERSTIM™ devices of Medtronic, Inc (Minneapolis, Minn.), the Finetech-Brindley bladder control system (Finetech Medical, Hertfordshire, UK) and the BION™ devices of Advanced Bionics Corp.

As used herein, "implanted" is taken to mean positioned within the patient's body. Partial implantation means that only part of the apparatus is implanted—i.e. only part of the apparatus is positioned within the patient's body, with other elements of the apparatus external to the patient's body. Wholly implanted means that the entire apparatus is positioned within the patient's body.

For the avoidance of doubt, the apparatus being "wholly implanted" does not preclude additional elements, independent of the apparatus but in practice useful for its functioning (for example, a remote wireless charging unit or a remote wireless manual override unit), being independently formed and external to the patient's body.

As used herein, "charge-balanced" in relation to a DC current is taken to mean that the positive or negative charge introduced into any system (e.g. a nerve) as a result of a DC current being applied is balanced by the introduction of the opposite charge in order to achieve overall (i.e. net) neutrality.

As used herein, a "pharmaceutical composition" is a composition suitable for administration to a subject or patient.

As used herein, a "compound for treating a calcitonin-associated disease" is taken to mean a pharmacological compound capable of treating a calcitonin-associated disease. Such compounds include a calcitonin (for example salmon calcitonin), an osteoclast inhibitor (for example a bisphosphonate (such as non-nitrogenous bisphosphonates (e.g. etidronate, clodronate, tiludronate) and/or nitrogenous bisphosphonates (e.g. pamidronate, neridronate, olpadronate, alendronate, ibandronate, risedronate, zoledronate)), calcium, vitamin D, a PTH (e.g. human PTH), raloxifene, strontium ranelate and an anti-RANKL antibody (e.g. denosumab).

In accordance with a first aspect, there is provided an apparatus for stimulating the neural activity of at least one superior laryngeal nerve (SLN) of a patient, the apparatus comprising: an actuator configured to apply a signal to said at least one SLN of the patient; and a controller coupled to the actuator, the controller controlling the signal to be applied by the actuator, such that the signal stimulates the neural activity of the SLN to produce a physiological response in the patient.

In certain embodiments, the physiological response produced in the patient is one or more of: an increase in circulating calcitonin, an increase in bone density, a decrease in bone resorption and/or an increase in bone formation. Methods of measuring these factors would be familiar to the skilled person.

Also provided is an apparatus for stimulating the neural activity of at least one cervical sympathetic trunk (CST) of a patient, the apparatus comprising: an actuator configured to apply a signal to said at least one CST of the patient; and a controller coupled to the actuator, the controller controlling the signal to be applied by the actuator, such that the signal stimulates the neural activity of the CST to produce a physiological response in the patient.

In certain embodiments, the physiological response produced in the patient is one or more of: a decrease in circulating calcitonin, a decrease in circulating T4, an increase in circulating PTH, a decrease in bone density, an increase in bone resorption and/or a decrease in bone formation. Methods of measuring these factors would be familiar to the skilled person.

The following embodiments relate equally and independently to apparatuses for stimulating the neural activity of a SLN of a patient for and also to apparatuses for stimulating the neural activity of a CST of a patient, except where indicated otherwise.

In certain embodiments, the stimulation of the neural activity of the nerve is stimulation of the myelinated fibres of the nerve. In certain embodiments, the stimulation of neural activity of the nerve is selective stimulation of the myelinated fibres of the nerve, for example of the SLN. A signal selectively stimulates the myelinated fibres if that signal results in a preferential increase in neural activity of the myelinated fibres of the nerve compared to in the unmyelinated fibres. Preferably, selective stimulation of the myelinated fibres of a subject nerve does not lead to an increase in neural signaling in the unmyelinated nerve fibres of the subject nerve.

In certain embodiments, the stimulation of neural activity of the nerve is stimulation of the large myelinated fibres, preferably selective stimulation. A signal selectively increases the signaling activity of the large myelinated fibres of the nerve if that signal results in a preferential increase in neural activity of the large myelinated fibres of the nerve compared to in the small myelinated fibres and unmyelinated fibres. Preferably, selective stimulation of the large myelinated fibres of a subject nerve does not lead to an increase in neural signaling in the small myelinated fibres and unmyelinated fibres of the subject nerve.

In certain embodiments, the signal applied by the one or more actuators is a non-destructive signal. As used herein, a "non-destructive signal" is a signal as defined above that, when applied, does not irreversibly damage the underlying neural signal conduction ability. That is, application of a non-destructive signal maintains the ability of the nerve or nerves (or fibres thereof) to conduct action potentials when application of the signal ceases, even if that conduction is in practice inhibited or blocked as a result of application of the non-destructive signal.

In those embodiments in which the apparatus has more than one actuator, the signal which each of the actuators is configured to apply is independently selected from the signal to be applied by the other actuator.

In certain embodiments, the signal which the actuator is configured to apply is of a modality selected from an electrical signal, an optical signal, an ultrasonic signal, and a thermal signal. In certain embodiments, the actuator may be comprised of one or more electrodes, one or more photon sources, one or more ultrasound transducers, one more sources of heat, or one or more other types of actuator arranged to put the signal into effect.

In certain embodiments, the actuator is an electrode and the signal applied by the actuator is an electrical signal, for example a voltage or current. In certain such embodiments the signal applied comprises a direct current (DC) waveform, such as a charge balanced direct current waveform, or an alternating current (AC) waveform, or both a DC and an AC.

In certain embodiments the signal comprises an AC or DC waveform having a frequency of 0.1-100 Hz, optionally 0.5-80 Hz, optionally 5-70 Hz, optionally 10-50 Hz, optionally 20-50 Hz, optionally 25-50 Hz, optionally 35-45 Hz, optionally 40 Hz. In certain embodiments, the signal is an electrical signal having a frequency of 10 Hz, 20 Hz or 40 Hz.

Typically, for signal application to be effective, the signal parameters should be appropriate. Signal parameters include the intensity (for example relative intensity "T", or current/voltage), the pulse duration, and frequency.

Relative signal intensity can be expressed as multiples (0.1, 0.8, 1, 2, 5, etc.) of "T". "T" is the threshold stimulation intensity required to evoke a motor response in the cricothyreoidus muscle.

By way of example, T may be determined as follows: a low frequency electrical signal, typically 1 Hz, is applied to the nerve and the intensity of stimulation is increased (either by increasing the voltage or the current of the signal, preferably the current) until the signal produces a response in the cricothyreoidus. This response can be determined by means known to the skilled person—for example visually or by EMG measurement. The stimulation intensity required to induce a response is designated T. The absolute threshold stimulation intensity may vary across individuals, and subsequent experimental or therapeutic intensities are designated as multiples of T to provide equivalent relative stimulation intensities.

The desired stimulation intensity (i.e. the desired multiple of threshold intensity "T") can be achieved through controlled variation of the current or voltage of the signal, preferably the current.

For example, if the stimulation threshold is identified to be 0.2V, 1T is 0.2V and 50T is 10 V.

In certain embodiments the electrical signal has an intensity of from 0.1T to 50T, optionally 0.1 T to 20 T, for example 0.1-5.0T. In certain embodiments, the electrical signal has a signal intensity of 0.1T-5.0T, optionally 0.5-3.0T, optionally 1.0-2.5T, optionally 2T. In certain preferred embodiments the signal has a T value of 2T. In certain embodiments, the signal has an intensity of 20T.

In certain embodiments, the electrical signal has a pulse width of 0.01 ms-2 ms, optionally 0.05-1 ms, optionally 0.1-0.8 ms, optionally 0.5 ms. It was identified that for electrical signals having a pulse width of 0.5 ms, the current intensity required to achieve threshold stimulation was ten times lower than the current intensity required to achieve threshold stimulation when the pulse width was 0.01 ms. A pulse width of 0.1-0.8 ms, preferably 0.5 ms is therefore particularly advantageous as it reduces the required current intensity.

In certain embodiments, the electrical signal is AC or DC and has a square waveform, a rectangular waveform, a sinusoidal waveform, a triangular waveform or a sawtoothed waveform. In certain preferred embodiments, the electrical signal has a rectangular waveform, preferably a DC rectangular waveform. In certain alternative embodiments, the waveform is a biphasic waveform.

In certain preferred embodiments, the signal is an electrical signal comprising an AC or DC waveform of 40 Hz 2T.

In certain embodiments wherein the signal applied by the one or more actuators is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In those embodiments in which the signal applied by the one or more actuators is a thermal signal, at least one of the one or more actuators is configured to apply a thermal signal. In such embodiments, one or more of the one or more actuators may comprise a Peltier element configured to apply a thermal signal, optionally all of the one or more actuators comprise a Peltier element. In certain embodiments, the actuator may comprise a laser diode configured to apply a thermal signal, (e.g. a diode configured to emit infrared radiation). In certain embodiments, the actuator may comprise an electrically resistive element configured to apply a thermal.

In certain embodiments the signal applied by the one or more actuators is a mechanical signal, optionally an ultrasonic signal. In such embodiments, the actuator configured to apply the signal is an ultrasound actuator. In certain alternative embodiments, the mechanical signal applied by the one or more actuators is a pressure signal.

In certain embodiments the signal applied by the one or more actuators is an electromagnetic signal, optionally an optical signal. In certain such embodiments, the actuator may comprise a laser and/or a light emitting diode configured to apply the optical signal. In some embodiments, the apparatus further comprises a fibre optic interface configured to apply said signal from said one or more of the actuators to said at least one nerve.

It will be appreciated that in embodiments in which the apparatus comprises more than one actuator, the signal to be applied by each actuator is independently selected from the signal applied by the other actuator(s).

In certain embodiments, the apparatus further comprises one or more detector elements configured to detect the one or more physiological parameters. That is, in such embodiments each detector may detect more than one physiological parameter, for example all the detected physiological parameters. Alternatively, in such embodiments each of the one or more detector elements is configured to detect a separate parameter of the one or more physiological parameters detected.

In certain embodiments, the one or more detected physiological parameters are selected from: sympathetic tone, parasympathetic tone, circulating calcitonin, circulating T4, circulating T3, and/or circulating PTH. In addition, the one or more detected physiological parameters may be selected from: nerve activity in a SLN, a CST nerve or a vagal nerve.

In such embodiments, the controller is coupled to the detector element configured to detect one or more physiological parameters, and causes the actuator or actuators to apply the signal when the physiological parameter is detected to be meeting or exceeding a predefined threshold value.

It will be appreciated that any two or more of the indicated physiological parameters may be detected in parallel or consecutively. For example, in certain embodiments, the controller is coupled to a detector or detectors configured to detect the pattern of action potentials in the SLN at the same time as the blood calcium level in the patient.

In certain embodiments, the stimulation in neural activity as a result of applying the signal is stimulation of neural activity in at least myelinated fibres of the nerve to which the signal is applied. In certain embodiments, neural activity is increased across the whole nerve. In certain preferred embodiments, neural activity is selectively stimulated in the myelinated fibres of the nerve to which the signal is applied (e.g. the SLN). In certain embodiments, neural activity is selectively stimulated in the large myelinated fibres of the nerve to which the signal is applied (e.g. the SLN).

In certain embodiments, the result of applying the signal is an alteration to the pattern of action potentials in the nerve to which the signal is applied. In certain such embodiments, the neural activity is modulated such that the resultant pattern of action potentials in the nerve resembles the pattern of action potentials in the nerve or nerves observed in a healthy subject.

In certain embodiments, the controller causes the signal to be applied intermittently. In certain such embodiments, the controller causes the signal to applied for a first time period, then stopped for a second time period, then reapplied for a third time period, then stopped for a fourth time period. In such an embodiment, the first, second, third and fourth periods run sequentially and consecutively.

The series of first, second, third and fourth periods amounts to one application cycle. In certain such embodiments, multiple application cycles can run consecutively such that the signal is applied in phases, between which phases no signal is applied. In certain embodiments, the signal applied for the first time period and the signal applied for the third time period are of the same parameters (frequency, amplitude, etc.) and the same modality. In other embodiments, the signal applied for the first and third time periods are of different parameters, and/or different modality.

In such embodiments, the duration of the first, second, third and fourth time periods is independently selected. That is, the duration of each time period may be the same or different to any of the other time periods. In certain such embodiments, the duration of each of the first, second, third and fourth time periods is independently any time from 0.5 seconds (0.5 s) to 24 hours (24 h), is to 18 h, 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 1 s, 2 s, 3 s, 4 s, 5 s, 6 s, 8 s, 9 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain preferred embodiments, the first period is 0.1-5 s, optionally 0.2-3 s, optionally 0.5-2 s, optionally 1 s; the second period is 1-60 s, optionally 2-30 s, optionally 3-10 s, optionally 4 s or 8 s; the third period is 0.1-5 s, optionally 0.2-3 s, optionally 0.5-2 s, optionally 1s; the fourth period is 1-60 s, optionally 2-30 s, optionally 3-10 s, optionally 4 s or 8 s. In certain preferred embodiments, the first and third periods are equal and the second and fourth periods are equal. In other terms, in certain embodiments the signal is applied intermittently in cycles of 0.1-5 s on and 1-60 s off, optionally cycles of 0.2-3 s on and 2-30 s off, optionally cycles of 0.5-2 s on and 3-10 s off, optionally is on and 4 s off or is on and 8 s off. Such embodiments are particularly advantageous because the effect achieved by such intermittent signal application is similar to the effect observed with continuous signal application, but would reduce the energy required and therefore prolong battery life, for example.

In certain embodiments wherein the controller causes the signal to be applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the controller causes the signal to be applied intermittently, the signal is applied only when the patient is in a specific physiological state. In certain such embodiments, the signal is applied only when the patient exhibits a particular blood calcium level or circulating calcitonin level.

In certain such embodiments, the apparatus further comprises a communication, or input, element via which the status of the patient can be indicated by the patient or a physician. In alternative embodiments as already described, the apparatus further comprises a detector configured to detect the status of the patient, wherein the signal is applied only when the detector detects that the patient is in the specific state.

In certain embodiments of the apparatus, the stimulation in neural activity caused by the application of the signal is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to modulation.

In certain alternative embodiments, the stimulation in neural activity caused by the application of the signal or signals is substantially persistent. That is, upon cessation of the signal, neural activity in the nerve or nerves remains substantially the same as when the signal was being applied—i.e. the neural activity during and following modulation is substantially the same.

In certain embodiments, the stimulation in neural activity caused by the application of the signal is partially corrective, preferably substantially corrective. That is, upon cessation of the signal, neural activity in the nerve or nerves more closely resembles the pattern of action potentials in the nerve(s) observed in a healthy subject than prior to the signal being applied, preferably substantially fully resembles the pattern of action potentials in the nerve(s) observed in a healthy subject. For example, application of the signal may result in an increase in neural activity, and upon cessation of the signal, the pattern of action potentials in the nerve or nerves resembles the pattern of action potentials observed in a healthy individual.

In certain embodiments, the apparatus is suitable for at least partial implantation into the patient. In certain such embodiments, the apparatus is suitable to be fully implanted in the patient.

In certain embodiments, the apparatus further comprises one or more power supply elements, for example a battery, and/or one or more communication elements.

In a second aspect, is provided a method treating a calcitonin-associated disease in a patient comprising: implanting in the patient an apparatus according to the first aspect; positioning the actuator of the apparatus in signaling contact with a SLN of the patient; activating the apparatus. In certain embodiments, the method is a method for treating hyperthyroidism, osteoporosis, osteoarthritis or Paget's disease of bone. In certain embodiments, the method is a method for treating bipolar disorder or mania.

Also provided is a method of treating a thyroxine-associated disease, optionally hypothyroid syndrome, in a patient comprising: implanting in the patient an apparatus according to the first aspect; positioning the actuator of the apparatus in signaling contact with a CST of the patient; activating the apparatus. In certain embodiments, the method is a method of treating hypothyroid syndrome or Hashimoto's disease.

In such embodiments, the actuator is in signaling contact with the nerve when it is positioned such that the signal can be effectively applied to the nerve. The apparatus is activated when the apparatus is in an operating state such that the signal will be applied as determined by the controller.

In certain embodiments, the actuator positioned in signaling contact with the nerve applies a signal to stimulate neural activity in the myelinated fibres of the nerve, preferably to selectively stimulate the myelinated fibres of the nerve, preferably to selectively stimulate the large myelinated fibres of the nerve.

Implementation of all aspects of the invention (as discussed both above and below) will be further appreciated by reference to FIGS. 2A-2C.

Figure 2A:
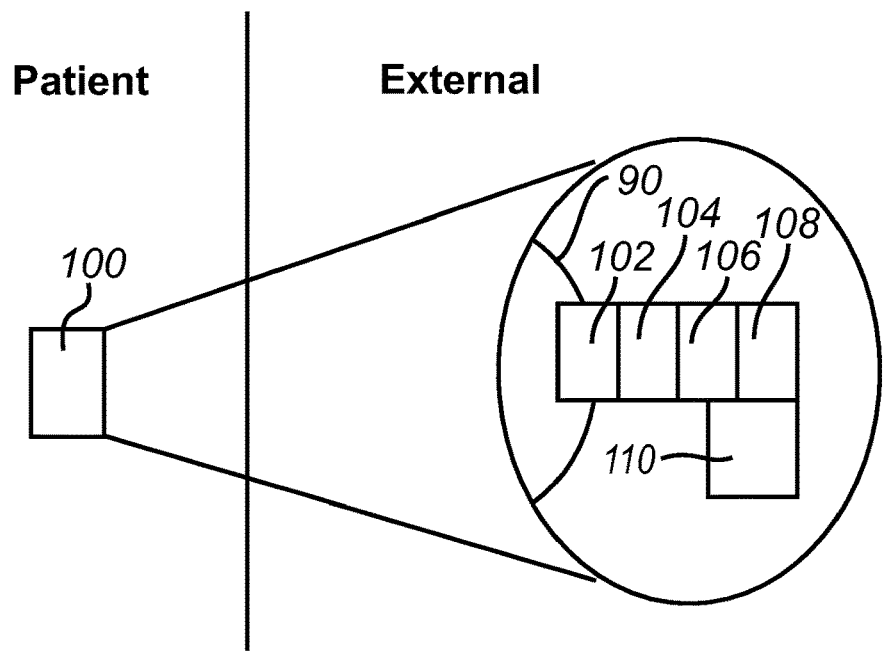
FIG. 2: Schematic drawings showing how apparatuses, devices and methods according to the invention can be put into effect.
Figure 2B:
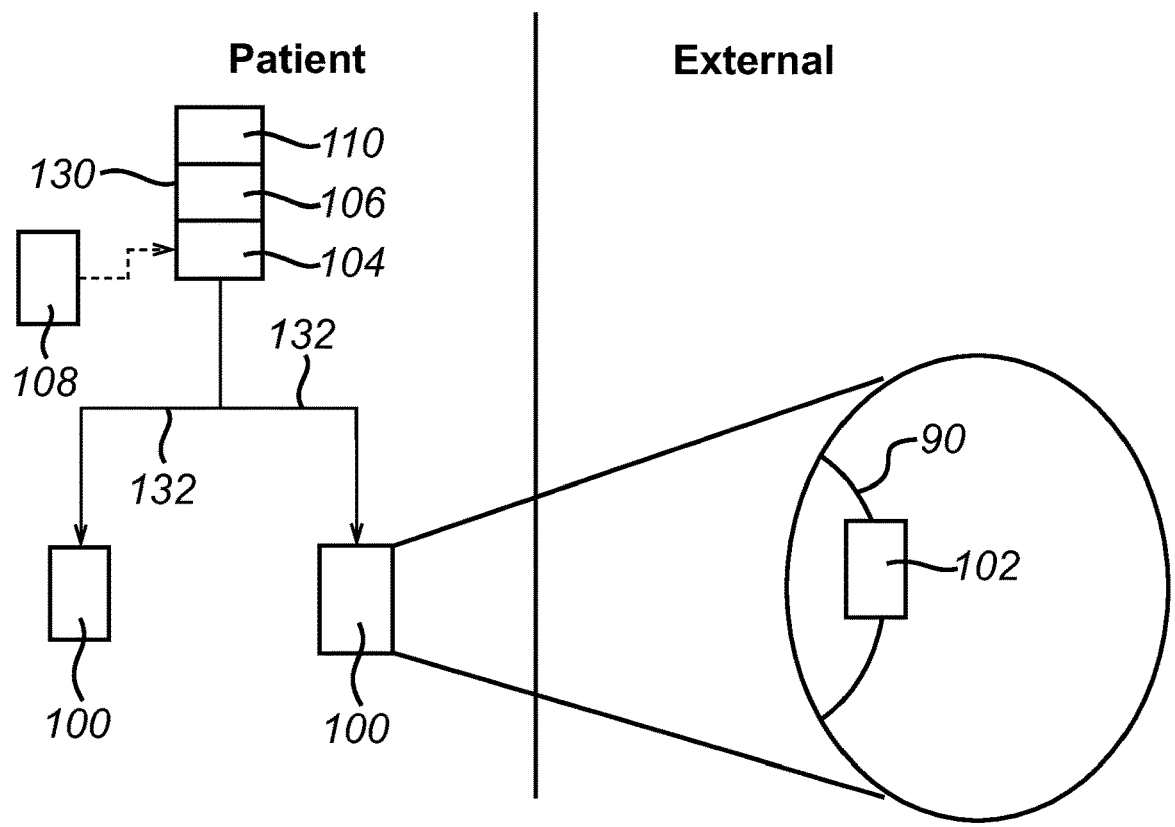
Figure 8A:
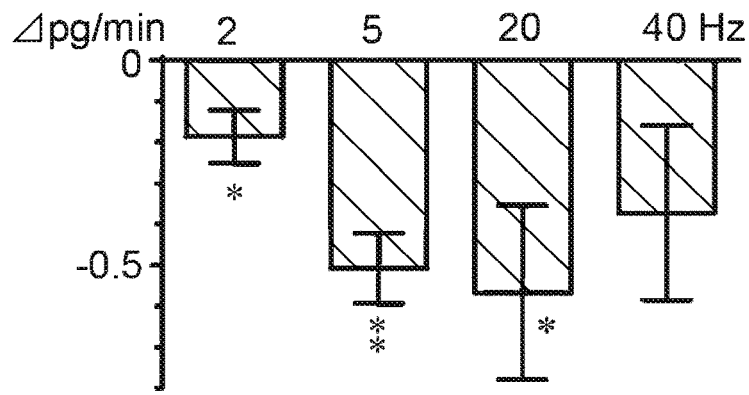
FIG. 8: Changes in iCT secretion rate during stimulation with the indicated parameters of (A) cut CSTs, (B) cut SLNs, (C) intact SLNs. *p<0.05, **p<0.01 (significant differences were determined by comparison with the prestimulus values).
Figure 8B:
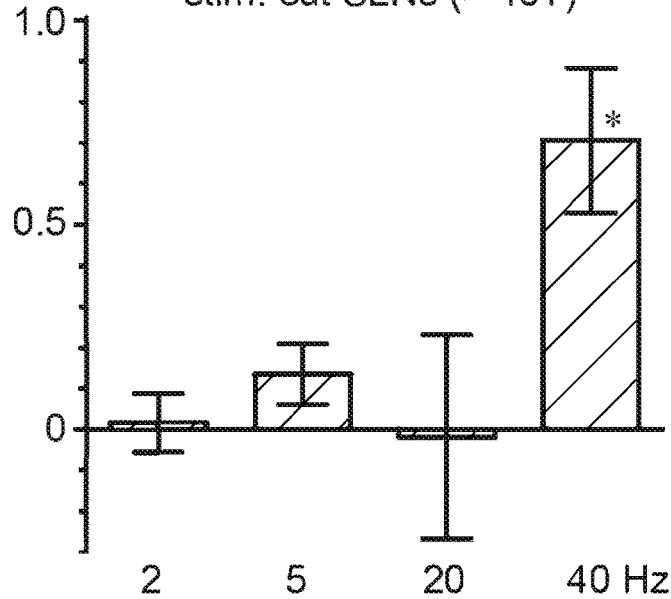
Figure 8C:
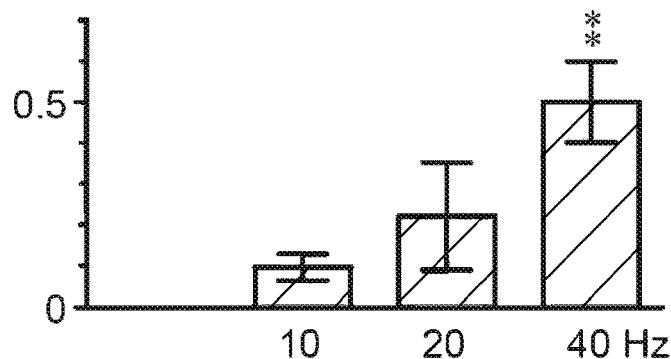
Figure 9A:
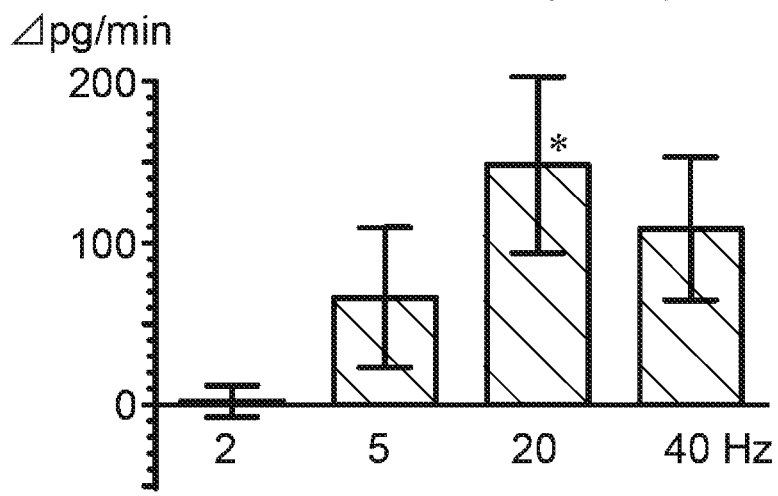
FIG. 9: Changes in iPTH secretion rate during stimulation with the indicated parameters of (A) cut CSTs, (B) cut SLNs, (C) intact SLNs. *p<0.05 (significant differences were determined by comparison with the prestimulus values).
Figure 9B:
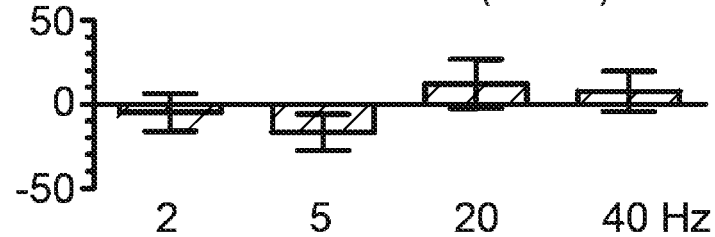
Figure 9C:
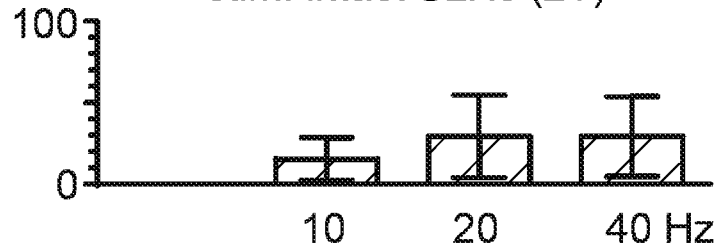
Figure 10A:
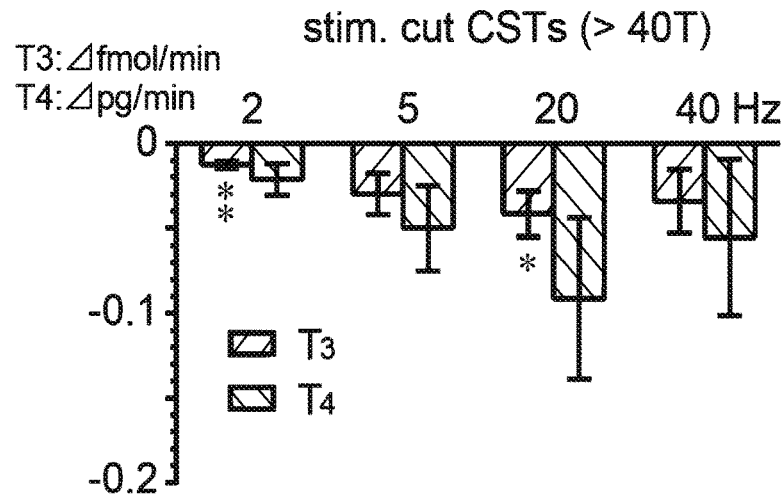
FIG. 10: Changes in iT3 (left paired bar) and iT4 (right paired bar) secretion rates during stimulation with the indicated parameters of (A) cut CSTs, (B) cut SLNs, (C) intact SLNs. *p<0.05, **p<0.01 (significant differences were determined by comparison with the prestimulus values).
Figure 10B:
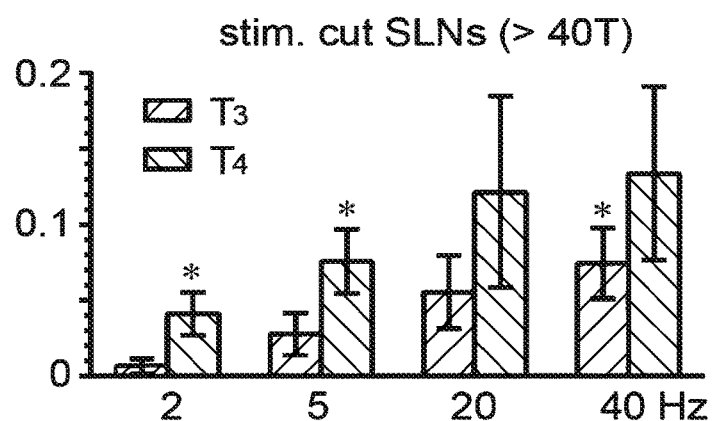
Figure 10C:
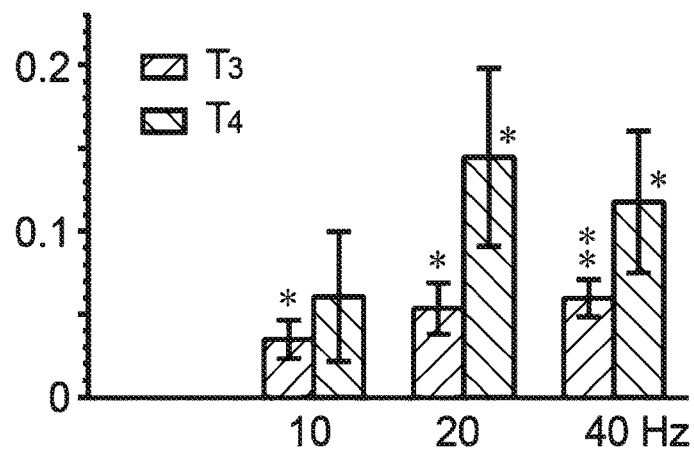

FIGS. 2A-2C show how the invention may be put into effect using one or more neuromodulation apparatuses which are implanted in, located on, or otherwise disposed with respect to a patient in order to carry out any of the various methods described herein. In this way, one or more neuromodulation apparatuses can be used to treat a calcitonin-associated disease or a thyroxine—associated disease in a patient, by modulating neural activity in a SLN or a CST, respectively.

In FIG. 2A a separate neuromodulation apparatus 100 is provided for unilateral neuromodulation, although as discussed above and below an apparatus could be provided for bilateral neuromodulation (100, FIGS. 2B and 2C). Each such neuromodulation apparatus may be fully or partially implanted in the patient, or otherwise located, so as to provide neuromodulation of the respective nerve or nerves. FIG. 2A also schematically shows in the cutaway components of one of the neuromodulation apparatuses 100, in which the apparatus comprises several elements, components or functions grouped together in a single unit and implanted in the patient. A first such element is an actuator 102 which is shown in proximity to a SLN 90 of the patient (the discussion below uses the SLN as an exemplary nerve, but the embodiments and arrangements described may apply equally to the CST). The actuator 102 may be operated by a controller element 104. The apparatus may comprise one or more further elements such as a communication element 106, a detector element 108, a power supply element 110 and so forth. Each neuromodulation apparatus 100 may operate independently, or may operate in communication with each other, for example using respective communication elements 106.

Each neuromodulation apparatus 100 may carry out the required neuromodulation independently, or in response to one or more control signals. Such a control signal may be provided by the controller 104 according to an algorithm, in response to output of one or more detector elements 108, and/or in response to communications from one or more external sources received using the communications element. As discussed herein, the detector element(s) could be responsive to a variety of different physiological parameters.

FIG. 2B illustrates some ways in which the apparatus of FIG. 2A may be differently distributed. For example, in FIG. 2B the neuromodulation apparatuses 100 comprise actuators 102 implanted proximally to a SLN 90, but other elements such as a controller 104, a communication element 106 and a power supply 110 are implemented in a separate control unit 130 which may also be implanted in, or carried by the patient. The control unit 130 then controls the actuators in both of the neuromodulation apparatuses via connections 132 which may for example comprise electrical wires and/or optical fibres for delivering signals and/or power to the actuators.

In the arrangement of FIG. 2B one or more detectors 108 are located separately from the control unit, although one or more such detectors could also or instead be located within the control unit 130 and/or in one or both of the neuromodulation apparatuses 100. The detectors may be used to detect one or more physiological parameters of the patient, and the controller element or control unit then causes the actuators to apply the signal in response to the detected parameter(s), for example only when a detected physiological parameter meets or exceeds a predefined threshold value. Physiological parameters which could be detected for such purposes include parasympathetic or sympathetic tone (neural, hemodynamic (e.g. heart rate, blood pressure, heart rate variability) or circulating plasma biomarkers) greater than a threshold parasympathetic or sympathetic tone; abnormal circulating calcitonin levels compared to a healthy individual, abnormal circulating T4 levels compared to a healthy individual, abnormal circulating T3 levels compared to a healthy individual, abnormal circulating PTH levels compared to a healthy individual, abnormal bone density levels compared to a healthy individual, abnormal SLN activity compared to a healthy individual, abnormal CST nerve activity levels compared to a healthy individual, and/or abnormal vagal nerve activity levels compared to a healthy individual.

A variety of other ways in which the various functional elements could be located and grouped into the neuromodulation apparatuses, a control unit 130 and elsewhere are of course possible. For example, one or more sensors of FIG. 2B could be used in the arrangement of FIG. 2A or 2C or other arrangements.

FIG. 2C illustrates some ways in which some functionality of the apparatus of FIG. 2A or 2B is provided not implanted in the patient. For example, in FIG. 2C an external power supply 140 is provided which can provide power to implanted elements of the apparatus in ways familiar to the skilled person, and an external controller 150 provides part or all of the functionality of the controller 104, and/or provides other aspects of control of the apparatus, and/or provides data readout from the apparatus, and/or provides a data input facility 152. The data input facility could be used by a patient or other operator in various ways, for example to input data relating to the activity status or blood calcium levels.

Each neuromodulation apparatus is adapted to carry out the stimulation required using one or more physical modes of operation involving applying a signal to a SLN, such a signal typically involving a transfer of energy to (or from) the nerve(s). As already discussed, such modes may comprise modulating the nerve or nerves using an electrical signal, an optical signal, an ultrasound or other mechanical signal, a thermal signal, a magnetic or electromagnetic signal, or some other use of energy to carry out the required modulation. Such signals may be non-destructive signals. Preferably the stimulation comprises stimulating, optionally selectively stimulating, neural activity in the myelinated fibres of the nerve, optionally selectively stimulating the large myelinated fibres of the nerve. To this end, the actuator 102 illustrated in FIG. 2A could be comprised of one or more electrodes, one or more photon sources, one or more ultrasound transducers, one more sources of heat, or one or more other types of actuators arranged to put the required stimulation into effect.

The neural modulation device(s) or apparatus may be arranged to stimulate (i.e. increase or induce) neural activity of a nerve, for example a SLN or CST, by using an actuator to apply a voltage or current, for example a direct current (DC) such as a charge balanced direct current, or an AC waveform, or both. The device or apparatus may be arranged to use the actuator(s) to apply an AC or DC waveform, preferably a DC waveform, having a frequency of 0.1-100 Hz, optionally 0.5-80 Hz, optionally 5-70 Hz, optionally 10-50 Hz, optionally 20-50 Hz, optionally 25-50 Hz, optionally 35-45 Hz, optionally 40 Hz. In certain embodiments, the signal is an electrical signal having a frequency of 10 Hz, 20 Hz or 40 Hz.

In certain embodiments the signal has an intensity of from 0.1T to 50T, optionally 0.5 T to 20 T, where "T" is the threshold stimulation intensity required to evoke a motor response in the cricothyreoidus muscle. The skilled person would be readily able to determine the appropriate value of T in any given patient.

In certain embodiments, the electrical signal has a T value of 0.1T-5.0T, optionally 0.5-3.0T, optionally 1.0-2.5T, optionally 2T. In alternative embodiments, the electrical signal has a value of 20T.

In certain embodiments, the electrical signal has a pulse width of 0.01 ms-2 ms, optionally 0.05-1 ms, optionally 0.1-0.8 ms, optionally 0.5 ms. It was identified that for electrical signals having a pulse width of 0.5 ms, the current intensity required to achieve threshold stimulation was ten times lower than the current intensity required to achieve threshold stimulation when the pulse width was 0.01 ms. A pulse width of 0.1-0.8 ms, preferably 0.5 ms is therefore particularly advantageous as it reduces the required current intensity.

In certain embodiments, the electrical signal is AC or DC and has a square waveform, a rectangular waveform, a sinusoidal waveform, a triangular waveform or a sawtoothed waveform. In certain preferred embodiments, the electrical signal has a rectangular waveform, preferably a DC rectangular waveform. In certain alternative embodiments, the waveform is a biphasic waveform.

In certain preferred embodiments, the signal is an electrical signal comprising an AC or DC waveform of 40 Hz 2T.

In certain embodiments the signal is applied intermittently in cycles of 0.1-5 s on and 1-60 s off, optionally cycles of 0.2-3 s on and 2-30 s off, optionally cycles of 0.5-2 s on and 3-10 s off, optionally 1 s on and 4 s off or 1 s on and 8 s off. Such embodiments are particularly advantageous because the effect achieved by such intermittent signal application is similar to the effect observed with continuous signal application, but would reduce the energy required and therefore prolong battery life, for example.

Optogenetics is a technique that genetically modifies cells to express photosensitive features, which can then be activated with light to modulate cell function. Many different optogenetic tools have been developed that can be used to modulate neural firing. A list of optogenetic tools to suppress neural activity has been compiled (Epilepsia. 2014 Oct. 9. doi: 10.1111/epi.12804. WONOEP appraisal: Optogenetic tools to suppress seizures and explore the mechanisms of epileptogenesis. Ritter L M et al., which is incorporated herein by reference). Acrylamine-azobenzene-quaternary ammonium (AAQ) is a photochromic ligand that blocks many types of K+ channels and in the cis configuration, the relief of K+ channel block inhibits firing (Nat Neurosci. 2013 Jul; 16(7):816-23. doi: 10.1038/nn.3424. Optogenetic pharmacology for control of native neuronal signaling proteins. Kramer R H et al, which is incorporated herein by reference). By adapting Channelrhodopsin-2 and introducing it into mammalian neurons with the lentivirus, it is possible to control synaptic transmission (Boyden E S 2005). Instead of using an external light source such as a laser or light emitting diode, light can be generated internally by introducing a gene based on firefly luciferase (Land BB 2014). The internally generated light has been sufficient to generate neural modulation.

Mechanical forms of neuromodulation can include the use of ultrasound which may conveniently be implemented using external instead of implanted ultrasound transducers. Other forms of mechanical neuromodulation include the use of pressure (for example see "The effects of compression upon conduction in myelinated axons of the isolated frog sciatic nerve" by Robert Fern and P. J. Harrison Br.j. Anaesth. (1975), 47, 1123, which is incorporated herein by reference).

Some electrical forms of neuromodulation may use signals applied by bipolar or tripolar electrodes. Commercially available bipolar cuff electrodes are available from Cor-Tec™. Other suitable forms of electrode include hook or wire electrodes which may be positioned on or adjacent to the target nerve.

In a third aspect, is provided a method of treating a calcitonin-associated disease in a patient, the method comprising applying a signal to a part or all of a SLN of said patient to stimulate neural activity in said nerve in the patient.

In certain embodiments, treatment of the calcitonin-associated disease is indicated by an improvement in a measurable physiological parameter, wherein said measurable physiological parameter is at least one of: an increase in circulating calcitonin, an increase in bone density, a decrease in bone resorption and/or an increase in bone formation. Suitable methods for determining the value for any given parameter would be appreciated by the skilled person.

In certain embodiments, the calcitonin associated disease is hyperthyroidism, osteoporosis, osteoarthritis or Paget's disease of bone. In certain embodiments, the calcitonin associated disease is bipolar disorder or mania.

In certain embodiments, the stimulation of neural activity as a result of applying the signal is an increase in neural activity in the myelinated fibres of the SLN, optionally wherein the result of applying the signal is a selective increase in neural activity in the myelinated fibres of the SLN, optionally wherein the result of applying the signal is a selective increase in neural activity in the large myelinated fibres of the SLN.

Also provided is a method of treating a thyroxine-associated disease in a patient, the method comprising applying a signal to a part or all of a CST of said patient to stimulate the neural activity of said nerve in the patient.

In certain embodiments, treatment of the thyroxine-associated disease is indicated by an improvement in a measurable physiological parameter, wherein said measurable physiological parameter is at least one of: a decrease in circulating calcitonin, a decrease in circulating T4, an increase in circulating PTH, a decrease in bone density, an increase in bone resorption and/or a decrease in bone formation. Suitable methods for determining the value for any given parameter would be appreciated by the skilled person.

In certain embodiments, the thyroxine-associated disease is hypothyroidism or Hashimoto's disease. In certain embodiments, the thyroxine-associated disease is depression. In certain embodiments, the thyroxine-associated disease is obesity.

In certain embodiments, the stimulation of neural activity as a result of applying the signal is an increase in neural activity in the myelinated fibres of the CST, optionally wherein the result of applying the signal is a selective increase in neural activity in the myelinated fibres of the CST, optionally wherein the result of applying the signal is a selective increase in neural activity in the large myelinated fibres of the CST.

The following embodiments apply equally and independently to the methods of treating a calcitonin-associated disease and to the methods of treating a thyroxine-associated disease, unless indicated otherwise.

In certain embodiments, the signal is applied by a neuromodulation apparatus comprising one or more actuators configured to apply the signal. In certain preferred embodiments the neuromodulation apparatus is at least partially implanted in the patient. In certain preferred embodiments, the neuromodulation apparatus is wholly implanted in the patient. For the avoidance of doubt, the apparatus being "wholly implanted" does not preclude additional elements, independent of the apparatus but in practice useful for its functioning (for example, a remote wireless charging unit or a remote wireless manual override unit), being independently formed and external to the patient's body.

In certain embodiments, the method is applied unilaterally. That is, in such embodiments the signal or signals are applied only to the left or only to the right SLN or CST nerve. In certain alternative embodiments, the method is applied bilaterally. That is, in such embodiments, a signal is applied to the left and to the right SLN or CST nerves.

In certain embodiments, the treatment of a calcitonin-associated disease or of a thyroxine-associated disease is prophylactic treatment. That is, the methods of the invention prevent the onset of the disease. For example, the method may prevent or ameliorate the onset of a disease in at risk patients. For example patients at risk of osteoporosis include those having diabetes, vitamin D deficiency, smokers, those patients with prolonged immobilisation, or those with a family history of osteoporosis. By way of further example, patients at risk of hypothyroidism include those having diabetes, iodine deficiency, celiac disease or systemic lupus erythematosus (SLE).

In certain embodiments, the treatment of a calcitonin-associated disease or of a thyroxine-associated disease is therapeutic treatment. That is, the methods of the invention at least partially reduce the signs and symptoms of the disease exhibited by the patient. For example, methods according to the invention may result in the patient exhibiting levels of bone formation, bone resorption, weight control or bone fractures closer to those levels of a healthy patient.

In certain embodiments, treatment of the condition is indicated by an improvement in the profile of neural activity in the nerve or nerves to which the signal is applied. That is, treatment of the condition is indicated by the neural activity in the nerve(s) approaching the neural activity in a healthy individual.

In certain preferred embodiments, the signal stimulates neural activity in the myelinated fibres of the nerve to which the signal is applied (e.g. the SLN). In certain preferred embodiments, the signal selectively stimulates neural activity in the myelinated fibres of the nerve to which the signal is applied (i.e. the SLN or CST). In certain preferred embodiments, the signal selectively stimulates neural activity in the large myelinated fibres of the nerve to which the signal is applied (i.e. the SLN or CST).

It will be appreciated by the skilled person that stimulation of neural activity in myelinated fibres may result in downstream reflex neural activity. Without wishing to be bound by theory, the changes in hormone secretion as a result of stimulating activity, for example in the SLN, may be mediated by the stimulation inducing reflex efferent neural activity. Inducing reflex efferent neural activity by selective stimulation of myelinated neural activity has the advantage that the signal intensity can be lower than for direct stimulation of efferent neural activity, thereby reducing potential damage to the target nerves. For the avoidance of doubt, reflex efferent neural activity is not considered part of the stimulation of neural activity as a result of the signal being applied—the modulation in neural activity is taken to be the activity directly caused by application of the signal, not any reflex response. For example, selective stimulation of myelinated fibres, optionally large myelinated fibres, of the SLN (for example by using lower amplitude and narrow pulse widths) would preferentially stimulate neural activity directly in the myelinated fibres, but may result in subsequent efferent activity in the nerve due to a reflex response. It is within the ability of the skilled person to differentiate between direct neuromodulation as a result of the signal being applied and that induced by a reflex response.

In certain embodiments, the signal is applied intermittently. In certain such embodiments, the signal is applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods is any from 0.5 seconds (0.5 s) to 24 hours (24 h), is to 18 h, 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 1s, 2 s, 3 s, 4 s, 5 s, 6 s, 8 s, 9 s, 10 s, 30 s, 60 s, 2 mM, 5 mM, 10 mM, 20 mM, 30 mM, 40 min, 50 min, 60 mM, 90 mM, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain preferred embodiments, the first period is 0.1-5 s, optionally 0.2-3 s, optionally 0.5-2 s, optionally 1 s; the second period is 1-60 s, optionally 2-30 s, optionally 3-10 s, optionally 4 s or 8 s; the third period is 0.1-5 s, optionally 0.2-3 s, optionally 0.5-2 s, optionally 1s; the fourth period is 1-60 s, optionally 2-30 s, optionally 3-10 s, optionally 4 s or 8 s. In certain preferred embodiments, the first and third periods are equal and the second and fourth periods are equal. In other terms, in certain embodiments the signal is applied intermittently in cycles of 0.1-5 s on and 1-60 s off, optionally cycles of 0.2-3 s on and 2-30 s off, optionally cycles of 0.5-2 s on and 3-10 s off, optionally is on and 4 s off or is on and 8 s off. Such embodiments are particularly advantageous because the effect achieved by such intermittent signal application is similar to the effect observed with continuous signal application, but would reduce the energy required and therefore prolong battery life, for example.

In certain embodiments wherein the signal is applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the controller causes the signal to be applied intermittently, the signal is applied only when the patient is in a specific physiological state. In certain such embodiments, the signal is applied only when the patient exhibits a particular blood calcium level or circulating calcitonin level.

In such embodiments, the status of the patient (e.g. their circulating calcitonin level) can be indicated by the patient. In alternative such embodiments, the status of the patient can be detected independently from any input from the patient. In certain embodiments in which the signal is applied by a neuromodulation apparatus, the apparatus further comprises a detector configured to detect the status of the patient, wherein the signal is applied only when the detector detects that the patient is in the specific state.

In certain embodiments of methods according to the invention, the method further comprises the step of detecting one or more physiological parameters of the patient, wherein the signal is applied only when the detected physiological parameter meets or exceeds a predefined threshold value. In such embodiments wherein more than one physiological parameter is detected, the signal may be applied when any one of the detected parameters meets or exceeds its threshold value, alternatively only when all of the detected parameters meet or exceed their threshold values. In certain embodiments wherein the signal is applied by a neuromodulation apparatus, the apparatus further comprises at least one detector element configured to detect the one or more physiological parameters.

In certain embodiments, the one or more detected physiological parameters are one or more of: sympathetic tone, parasympathetic tone, circulating calcitonin, circulating T4, circulating T3, and/or circulating PTH. The measurable physiological parameter may comprise an action potential or pattern of action potentials in one or more nerves of the patient, wherein the action potential or pattern of action potentials is associated with a calcitonin-associated disease or thyroxine-associated disease. Suitable nerves in which to detect an action potential or pattern of action potentials include a SLN, a CST nerve and/or a vagal nerve. In a particular embodiment, the measurable physiological parameter comprises the pattern of action potentials in an SLN.

It will be appreciated that any two or more of the indicated physiological parameters may be detected in parallel or consecutively. For example, in certain embodiments, the pattern of action potentials in an SLN can be detected at the same time as circulating calcitonin.

In certain alternative embodiments, the signal is permanently applied. That is, once begun, the signal is continuously applied to the nerve or nerves. It will be appreciated that in embodiments wherein the signal is a series of pulses, gaps between pulses do not mean the signal is not continuously applied.

In certain embodiments of the methods, the stimulation of neural activity caused by the application of the signal is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to stimulation.

In certain alternative embodiments, the stimulation of neural activity caused by the application of the signal is substantially persistent. That is, upon cessation of the signal, neural activity in the nerve or nerves remains substantially the same as when the signal was being applied—i.e. the neural activity during and following stimulation is substantially the same.

In certain embodiments, the stimulation of neural activity caused by the application of the signal is partially corrective, preferably substantially corrective. That is, upon cessation of the signal, neural activity in the nerve or nerves more closely resembles the pattern of action potentials observed in a healthy subject than prior to stimulation, preferably substantially fully resembles the pattern of action potentials observed in a healthy subject. By way of example, application of the signal may result in stimulation of neural activity, and upon cessation of the signal, the pattern of action potentials in the nerve resembles the pattern of action potentials observed in a healthy subject. It is hypothesised that such a corrective effect is the result of a positive feedback loop.

In certain such embodiments, once first applied, the signal may be applied intermittently or permanently, as described in the embodiments above.

In certain embodiments wherein the modulation is bilateral, each signal is applied by a single neuromodulation apparatus. In certain alternative embodiments, the left-side signal is applied by one neuromodulation apparatus and right-side signal is applied by another neuromodulation apparatus.

In certain embodiments, the signal applied is a non-destructive signal.

In certain embodiments of the methods according to the invention, the signal applied is an electrical signal, an electromagnetic signal (optionally an optical signal), a mechanical (optionally ultrasonic) signal, a thermal signal, a magnetic signal or any other type of signal.

In certain embodiments in which the signal is applied by a neuromodulation apparatus comprising at least one actuator, the actuator may be comprised of one or more electrodes, one or more photon sources, one or more ultrasound transducers, one more sources of heat, or one or more other types of actuator arranged to put the signal into effect.

In certain embodiments, the signal is an electrical signal, for example a voltage or current. In certain such embodiments the signal comprises a direct current (DC) waveform, such as a charge balanced DC waveform, or an alternating current (AC) waveform, or both a DC and an AC waveform. In certain embodiments, the signal comprises a DC waveform. In those embodiments in which the signal is an electrical signal and is applied by a neuromodulation apparatus, the actuator is an electrode, for example a cuff electrode.

In certain embodiments the signal comprises an AC or DC waveform having a frequency of 0.1-100 Hz, optionally 0.5-80 Hz, optionally 5-70 Hz, optionally 10-50 Hz, optionally 20-50 Hz, optionally 25-50 Hz, optionally 35-45 Hz, optionally 40 Hz. In certain embodiments, the signal is an electrical signal having a frequency of 10 Hz, 20 Hz or 40 Hz.

In certain embodiments the electrical signal has an intensity of from 0.1T to 50T, optionally 0.1 T to 20 T, for example 0.1-5.0T. In certain embodiments, the electrical signal has a signal intensity of 0.1T-5.0T, optionally 0.5-3.0T, optionally 1.0-2.5T, optionally 2T. In certain preferred embodiments the signal has a T value of 2T. In certain embodiments the signal has an intensity of 20T.

In certain embodiments, the electrical signal has a pulse width of 0.01 ms-2 ms, optionally 0.05-1 ms, optionally 0.1-0.8 ms, optionally 0.5 ms. It was identified that for electrical signals having a pulse width of 0.5 ms, the current intensity required to achieve threshold stimulation was ten times lower than the current intensity required to achieve threshold stimulation when the pulse width was 0.01 ms. A pulse width of 0.1-0.8 ms, preferably 0.5 ms is therefore particularly advantageous as it reduces the required current intensity.

In certain embodiments, the electrical signal is AC or DC and has a square waveform, a rectangular waveform, a sinusoidal waveform, a triangular waveform or a sawtoothed waveform. In certain preferred embodiments, the electrical signal has a rectangular waveform, preferably a DC rectangular waveform. In certain alternative embodiments, the waveform is a biphasic waveform.

In certain preferred embodiments, the signal is an electrical signal comprising an AC or DC waveform of 40 Hz 2T.

In certain embodiments wherein the signal is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In certain embodiments wherein the signal is a mechanical signal, the signal is an ultrasonic signal. In certain alternative embodiments, the mechanical signal is a pressure signal.

In certain preferred embodiments, the invention provides a method of treating a calcitonin-associated disease, optionally osteoporosis, the method comprising applying an electrical signal to a SLN of said patient to increase the neural activity of said nerve, preferably in the myelinated fibres of said nerve, preferably to selectively increase neural activity in the myelinated fibres of said nerve, preferably to selectively increase neural activity in the large myelinated fibres of said nerve, wherein the signal is applied by a neuromodulation apparatus at least partially implanted in the patient. In certain preferred embodiments, the electrical signal has a frequency of 40 Hz and an intensity of 2T. In certain preferred embodiments, the electrical signal is applied by a neuromodulation apparatus comprising an electrode arranged to apply the signal to the SLN.

In a fourth aspect is provided a neuromodulatory electrical waveform for use in treating a calcitonin-associated disease in a patient, wherein the waveform has a frequency of 10-50 Hz and intensity of 0.5T-5.0T, such that, when applied to a SLN of the patient, the waveform increases neural signaling in the SLN to which the signal is applied, preferably increases neural activity in the myelinated fibres of the SLN to which it is applied, preferably selectively increases neural activity in the myelinated fibres of the SLN to which it is applied, preferably selectively increases neural activity in the large myelinated fibres of the SLN to which it is applied.

In a fifth aspect is provided use of a neuromodulation apparatus for treating a calcitonin-associated disease in a patient by increasing neural activity in a SLN of the patient, preferably increasing neural activity in the myelinated fibres of the SLN, preferably selectively increasing neural activity in the myelinated fibres of the SLN, preferably selectively increasing neural activity in the large myelinated fibres of the SLN.

In a sixth aspect is provided for use in a method of treating a calcitonin-associated disease in a subject, wherein the composition comprises a compound for treating a calcitonin-associated disease, and wherein the method is a method according to the third aspect, the method further comprising the step of administering an effective amount of the pharmaceutical composition to the subject. It is a preferred embodiment that the pharmaceutical composition is for use in a method of treating a calcitonin-associated disease wherein the method comprises applying a signal to a SLN of said patient to stimulate the neural activity of said nerve in the patient, the signal being applied by a neuromodulation apparatus.

In a seventh aspect, the invention provides a pharmaceutical composition comprising a compound for treating a calcitonin-associated disease, for use in treating a calcitonin-associated disease in a subject, the subject having an apparatus according to the first aspect implanted. That is, the pharmaceutical composition is for use in treating a subject that has had an apparatus as described according to the first aspect implanted. The skilled person will appreciate that the apparatus has been implanted in a manner suitable for the apparatus to operate as described. Use of such a pharmaceutical composition in a patient having an apparatus according to the first aspect implanted will be particularly effective as it permits a cumulative or synergistic effect as a result of the combination of the compound for treating a calcitonin-associated disease and apparatus operating in combination.

In certain embodiments of the sixth or seventh aspect, the compound for treating a calcitonin-associated disease is selected from a calcitonin, an osteoclast inhibitor, calcium, vitamin D, a PTH, raloxifene, strontium ranelate and an anti-RANKL antibody.

In certain embodiments, the pharmaceutical composition may comprise a pharmaceutical carrier and, dispersed therein, a therapeutically effective amount of the compounds for treating a calcitonin-associated disease. The composition may be solid or liquid. The pharmaceutical carrier is generally chosen based on the type of administration being used and the pharmaceutical carrier may for example be solid or liquid. The compounds of the invention may be in the same phase or in a different phase than the pharmaceutical carrier.

Pharmaceutical compositions may be formulated according to their particular use and purpose by mixing, for example, excipient, binding agent, lubricant, disintegrating agent, coating material, emulsifier, suspending agent, solvent, stabilizer, absorption enhancer and/or ointment base. The composition may be suitable for oral, injectable, rectal or topical administration.

For example, the pharmaceutical composition may be administered orally, such as in the form of tablets, coated tablets, hard or soft gelatine capsules, solutions, emulsions, or suspensions. Administration can also be carried out rectally, for example using suppositories, locally or percutaneously, for example using ointments, creams, gels or solution, or parenterally, for example using injectable solutions.

For the preparation of tablets, coated tablets or hard gelatine capsules, the compounds for treating a calcitonin-associated disorder may be admixed with pharmaceutically inert, inorganic or organic excipients. Examples of suitable excipients include lactose, maize starch or derivatives thereof, talc or stearic acid or salts thereof. Suitable excipients for use with soft gelatine capsules include, for example, vegetable oils, waxes, fats and semi-solid or liquid polyols.

For the preparation of solutions and syrups, excipients include, for example, water, polyols, saccharose, invert sugar and glucose. For injectable solutions, excipients include, for example, water, alcohols, polyols, glycerine and vegetable oil. For suppositories and for local and percutaneous application, excipients include, for example, natural or hardened oils, waxes, fats and semi-solid or liquid polyols.

The pharmaceutical compositions may also contain preserving agents, solublizing agents, stabilizing agents, wetting agents, emulsifiers, sweeteners, colorants, odorants, buffers, coating agents and/or antioxidants.

Thus, a pharmaceutical formulation for oral administration may, for example, be granule, tablet, sugar coated tablet, capsule, pill, suspension or emulsion. For parenteral injection for, for example, intravenous, intramuscular or subcutaneous use, a sterile aqueous solution may be provided that may contain other substances including, for example, salts and/or glucose to make to solution isotonic. The compound may also be administered in the form of a suppository or pessary, or may be applied topically in the form of a lotion, solution, cream, ointment or dusting powder.

In an eighth aspect the invention provides a neuromodulation system, the system comprising a plurality of apparatuses according to the first aspect. In such a system, each apparatus may be arranged to communicate with at least one other apparatus, optionally all apparatuses in the system. In certain embodiments, the system is arranged such that, in use, the apparatuses are positioned to bilaterally modulate the neural activity of the myelinated fibres of the SLNs of a patient, preferably the large myelinated fibres of the SLNs of a patient. In certain embodiments, the system is arranged such that, in use, the apparatuses are positioned to unilaterally modulate the neural activity of the myelinated fibres of the SLNs of a patient, preferably the large myelinated fibres of the SLNs of a patient.

In such embodiments, the system may further comprise additional components arranged to communicate with the apparatuses of the system, for example a processor, a data input facility, and/or a data display module. In certain such embodiments, the system further comprises a processor. In certain such embodiments, the processor is comprised within a mobile device (for example a smart phone) or computer.

In a preferred embodiment of all aspects of the invention, the subject or patient is a mammal, more preferably a human. In certain embodiments, the subject or patient is suffering from a calcitonin-associated disease or thyroxine-associated disease, as appropriate.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

INCORPORATION BY REFERENCE

All documents and articles cited herein are incorporated by reference in their entirety.

The aspects, embodiments and implementation of the invention will be further understood by reference to the following non-limiting Examples. Alternatives according to the spirit of the invention will be appreciated by the skilled person.

EXAMPLES

Example 1

Effect of Stimulating SLN and CST Nerves on Thyroid Hormone Secretion

The effect of stimulation of autonomic (both sympathetic and parasympathetic) nerves at various frequencies on secretion of CT and PTH, together with T3 and T4, from thyroid and parathyroid glands in anesthetized rats was examined. In a first experiment (Example 1), cut peripheral end of the CSTs and SLNs were electrically stimulated with supramaximal strength of all nerve fibres. A second experiment (Example 2) examined whether selective activation of myelinated fibres in the SLN produces changes in hormonal secretion, possibly via reflex mechanisms. In this experiment, intact SLNs were stimulated electrically with a current intensity much lower than the threshold intensity for unmyelinated fibres.

Materials and Methods

The experiments were performed in 19 male Sprague Dawley rats (500-650 g, 4-7 months old) purchased from Japan SLC, Inc. The rats were used for three different experiments as summarized in Table 1. To determine effect of activation of unmyelinated nerve fibres (most likely efferent fibres), we performed experiments of stimulating cut peripheral end of CSTs (n=6) or SLNs (n=6). We also performed experiments of stimulating intact SLNs (n=7).

TABLE 1

| Experiment Group | Cut | Stimulation | Stimulus strength | Target fibres | n |
|---|---|---|---|---|---|
| Group-1 | CSTs | CSTs (cut peripheral ends) | 0.5 ms, 10 V (50 T) | Unmyelinated | 6 |
| Group-2 | SLNs | SLNs (cut peripheral ends) | 0.5 ms, 10 V (50 T) | Unmyelinated | 6 |
| Group-3 | Non | SLNs (intact) | 0.5 ms, 5-60 µA (2T) | Myelinated | 7 |

Experiments were performed under halothane (1.5-2% during surgery, 1.0% during experiments) or urethane (initially 1.1 g/kg. i.p., additional doses were added when necessary) anaesthesia. There was no difference between data obtained under different anaesthesia. Therefore, all data were combined. Respiration was maintained by an artificial respirator (SN-480-7; Shinano Seisakusho, Tokyo, Japan) through a tracheal cannula. Artificial respiration was adjusted to maintain the end-tidal $CO_2$ at 3-4% (Microcap; Oridion Medical, Jerusalem, Israel). Systemic arterial blood pressure was monitored through a catheter kept in a femoral artery. Any necessary drugs and fluids were injected through a catheter kept in a femoral vein. The body temperature monitored in the rectum was maintained between 37.0-38.0 oC by means of a direct current heating pad and an infrared lamp (ATB-1100; Nihon Kohden, Tokyo, Japan).

Stimulation of Autonomic Nerve Fibres

Figure 12A:
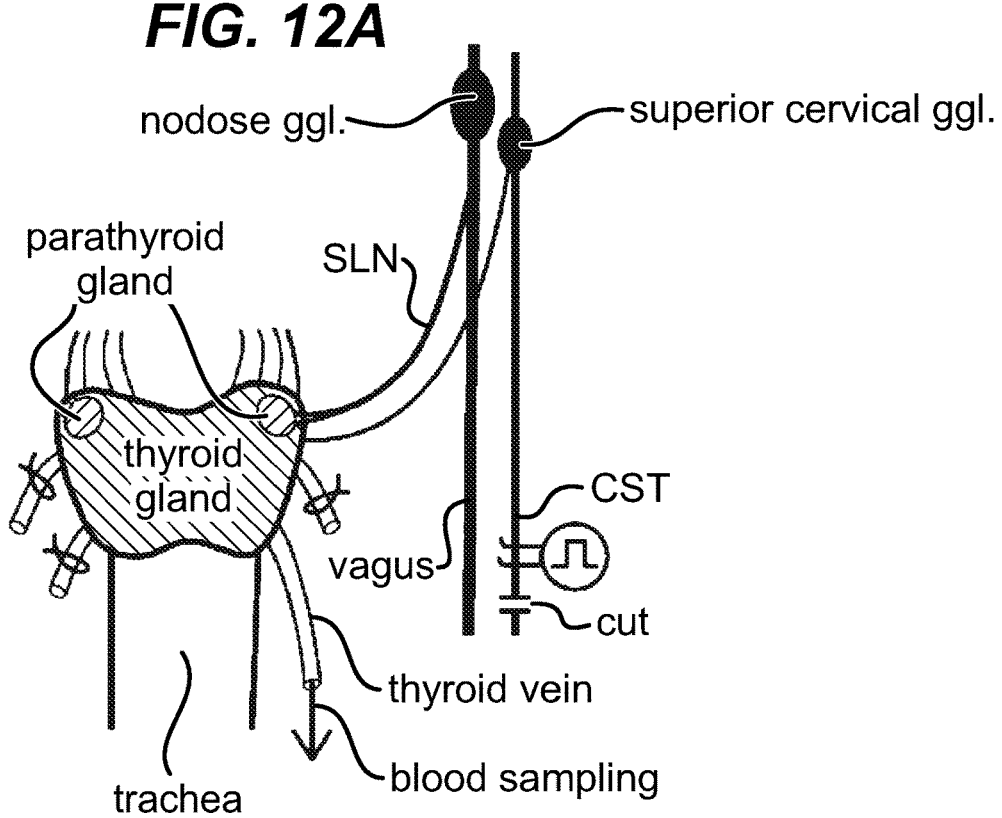
FIG. 12: Schematic diagram of the sympathetic (cervical sympathetic trunk: CST) and parasympathetic (superior laryngeal nerve: SLN) innervation of thyroid and parathyroid glands and the arrangements of stimulating electrodes according to some embodiments. Only the left CST and SLN are drawn for clarity, but experimental preparations were stimulated bilaterally. (A) Stimulation of cut CST ends by hook electrodes; (B) Stimulation of cut SLN ends by hook electrodes; (C) Stimulation of intact SLNs by cuff electrodes.
Figure 12B:
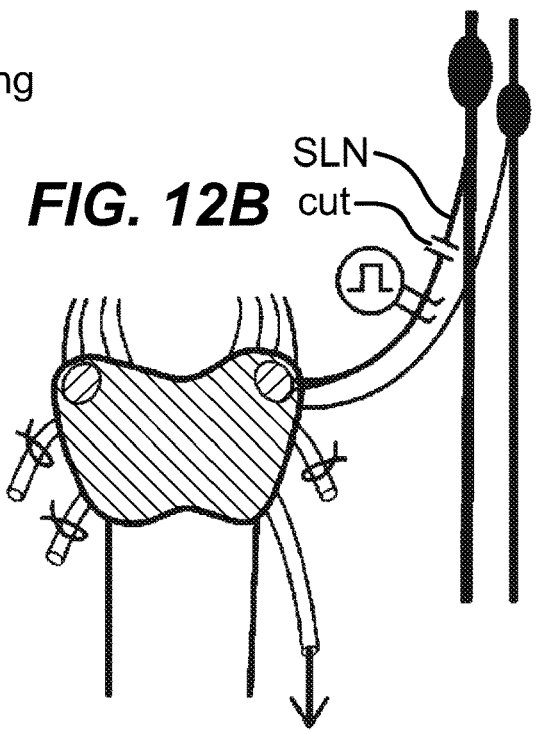

In order to stimulate the sympathetic nerve fibres innervating thyroid and parathyroid glands, the CSTs were cut bilaterally as caudal as possible in the neck. The peripheral (rostral) ends of these nerves were placed on bipolar, platinum-iridium wire electrodes (FIG. 12A). In order to stimulate the parasympathetic nerve fibres innervating thyroid and parathyroid glands, the SLNs were cut bilaterally at a site close to the nodose ganglia. The peripheral ends of these nerves were placed on bipolar, platinum-iridium wire electrodes (FIG. 12B). Stimulation was applied with rectangular pulses by an electric stimulator (SEN-7203; Nihon Kohden) and stimulus isolation unit (SS-202J; Nihon Kohden). The stimulus frequency was varied, but stimulus intensity and pulse duration were kept constant at 10 V and 0.5 ms, respectively, equivalent to 50T (1T was determined to by 0.2V, therefore 10V corresponds to 50T). The preliminary experiments confirmed that this intensity was a supramaximal for activating all unmyelinated fibres in both CSTs and SLNs. Additional experiments conducted at 20T showed that this intensity was also supramaximal for activating all unmyelinated fibres in both CSTs and SLNs.

Figure 12C:
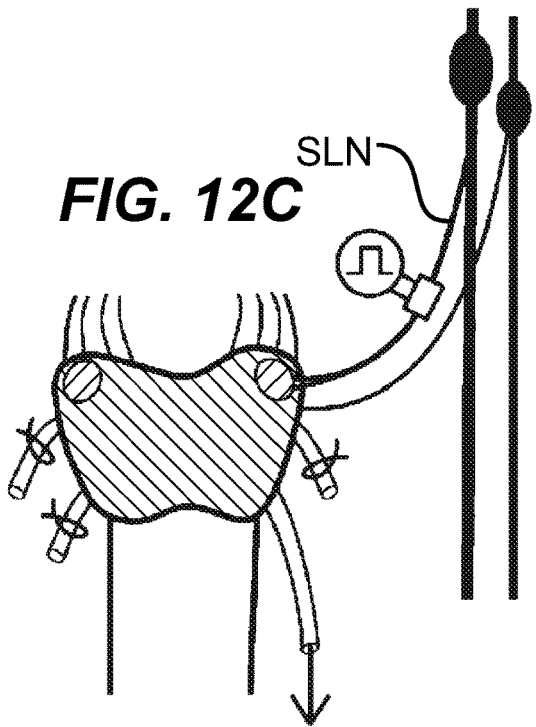

In order to stimulate the intact SLNs, we used cuff electrodes (CorTec, diameter 200 μm) (FIG. 12C). After setting cuff electrodes central from thyroid gland, we tested single 0.5 ms-pulse stimulation of various current intensities to each of right and left SLN and determined threshold intensity to evoke visible twitch of cricothyroid muscle. The stimulus frequency was varied, but stimulus intensity and pulse duration were kept constant at 2 times of the threshold (2T) intensity. The preliminary experiments confirmed that 2T was subthreshold for unmyelinated fibers, but enough to produce nearly maximum vasodilation due to activating myelinated fibres in SLNs. (Stimulation of cut peripheral end of SLNs produced vasodilative response above 10T).

Stimulation was applied by an electric stimulator (SEN-7203; Nihon Kohden) and stimulus isolation unit (SS-202J; Nihon Kohden). The nerves were kept in warm liquid paraffin to protect them from drying. Different frequencies, in a range of 0.5-40 Hz, were tested in each rat. Order of stimulus frequency was randomized to ensure the effects were not related to bleeding due to blood sampling.

Collecting Blood Samples

The thyroid gland was exposed from the ventral side, and one end of a thin polyethylene catheter (outer diameter of tip: approx. 0.3 mm) was inserted into a branch of thyroid veins, and all other remaining venous branches at both right and left sides were tied with thin threads, as described in previous papers (Ito et al., 1987; Kurosawa et al., 1988; Hotta et al., 1991), and then the animals were heparinized. One branch of the catheter was connected to the catheter inserted into a subclavian vein until sampling of thyroid venous blood was started. After waiting at least for 30 min under resting condition, a thyroid venous blood samples of 200-250 μl was collected in ice-chilled polyethylene tube through the thyroid venous catheter. We collected consecutively 13-16 thyroid venous blood samples in each experiment. In each rat, we delivered 4-5 different stimulations. For each stimulation, 3 blood samples were taken before, during and after stimulation. Dead volume of the thyroid venous catheter at the onset of each stimulus was collected to a capillary tube to measure hematocrit. A systemic arterial blood sample of about 250 μl was collected into the polyethylene tube through the femoral arterial catheter used for monitoring blood pressure at the beginning and the end of thyroid venous blood sampling. The systolic blood pressure was constantly maintained above 80 mmHg by infusing 4% Ficoll 70 in heparinized bicarbonate buffer solution through a femoral venous catheter during thyroid venous blood sampling, at a speed of 3.0 ml/h.

Blood samples were centrifuged within 30 min after collection, at 3000 rpm for 15 min at 4° C., plasma samples were collected and ethylene diamine tetraacetate disodium was added (2-4 mg/ml plasma). The samples were frozen and stored at −20° C. until assay. The thyroid venous blood plasma flow rate was calculated from the plasma volume of the thyroid venous blood sample and the sampling time.

Measurement of iCT, iPTH, iT3, and iT4

The concentrations of immunoreactive CT (iCT), PTH (iPTH), T3 (iT3) and T4 (iT4) in both thyroid venous blood plasma and systemic arterial blood plasma were measured by means of the ELISA method. We used kits for iCT (rat CT ELISA kit, MBS703165, MyBiosource, San Diego, USA), for iPTH (rat intact PTH ELISA kit, 60-2500, Immutopics, San Clemente, USA), and for iT3 (rat free T3 ELISA kit, CUSABIO, CSB-E05076r, Baltimore, USA), and iT4 (general free T4 ELISA Kit, USCN LIFE CEA185GE, Houston, Tex., USA). Thawed plasma samples were centrifuged for 2 min at 4,000 rpm at 4oC before assay. For each kit, at first we confirmed generation of a displacement curve by serial dilution of the thyroid venous plasma, and determined dilution rate (3-10 times). The secretion rate of each hormone was calculated from both plasma concentrations and plasma flow, as described previously (Ito et al., 1987; Kurosawa et al., 1988; Hotta et al., 1991), and the calculation is shown below:

Secretion rate=(concentration in thyroid venous plasma−concentration in systemic arterial plasma)×thyroid venous plasma flow rate.

Statistical Analysis

Values are expressed as mean±standard error. Statistical analysis for response was performed using two-way repeated ANOVA followed by Fischer's least significant difference test. Statistical analysis for basal values in three different conditions (CSTs cut, SLNs cut, and nerves intact) was performed using one-way factorial ANOVA followed by Dunnett's multiple comparison test. Statistical significance was set at the 5% level.

Results

Basal secretion rates of iCT, iPTH, iT3 and iT4 measured without stimulation in three different experimental groups were summarized in Table 2. The value was varied in each experiment, but was stable in individual animal throughout experiment. Hematocrit was gradually decreased, but was above 40% throughout experiments in all rats tested. The systemic arterial blood pressure was also stable under the resting condition throughout experiments. 1T was 2-30 μA in 14 SLNs in 7 rats, and also confirmed to be 0.2 V in 2 rats.

TABLE 2

| Hormones | CST cut | SLN cut | Nerves intact |
| --- | --- | --- | --- |
| iCT (pg/min) | 0.50 ± 0.08* | 0.37 ± 0.09 | 0.19 ± 0.05 |
| iPTH (pg/min) | 94 ± 43 | 52 ± 30 | 27 ± 19 |
| iT3 (fmol/min) | 0.081 ± 0.016 | 0.054 ± 0.013 | 0.059 ± 0.010 |
| iT4 (pg/min) | 0.15 ± 0.06 | 0.09 ± 0.02 | 0.10 ± 0.03 |
| plasma flow (μl/min) | 24 ± 5* | 13 ± 2 | 13 ± 1 | iCT Secretion
Basal Level

Basal secretion rates of iCT at rest without any nerve stimulation ranged from 0.1 to 0.8 pg/min in all cases tested, and were 0.50+0.08 pg/min (n=6), 0.37+0.09 pg/min (n=6), and 0.19+0.05 pg/min (n=7) in CST cut, SLN cut, and intact nerve condition, respectively (Table 2). Basal secretion rate of iCT in rats with CSTs cut was significantly higher (P<0.05) than that in nerves intact rats. However, the value in rats with SLNs cut was not significantly different from that in nerves intact rats.

Response to Nerve Stimulation iCT secretion decreased during CST stimulation, whereas increased during SLN stimulation. FIG. 3 summarizes the changes in iCT secretion measured consecutively before, during and after the end of stimulation. Stimulation of the cut peripheral end of CSTs at 5 Hz significantly (p<0.05) decreased iCT secretion, whereas stimulation of SLNs at 40 Hz, either cut peripheral end or intact nerve, significantly (p<0.01) increased iCT secretion during stimulation. All of these changes returned to the prestimulus level after the end of stimulation. The duration of stimulation varied between 4-11 min, depending on blood flow rate during stimulation (15-70 μl/min). The response was observed consistently in all rats tested. The magnitude of response was approximately 70% decrease during cut CST stimulation, 230% increase during cut SLN stimulation, and 380% increase during intact SLN stimulation, comparing to the corresponding prestimulus control values.

The response of iCT secretion was expressed as delta changes from prestimulus control values and frequency dependent changes in iCT secretion were summarized (FIG. 4). 2 Hz stimulation of cut CSTs or SLNs did not produce any significant changes in iCT secretion. Significant decrease was observed at 5-20 Hz during CST stimulation. However, the response attenuated at further increased frequency of 40 Hz (FIG. 4A). On the contrary, SLN stimulation increased iCT secretion selectively at 40 Hz, but not at 5-20 Hz, in either applied to cut peripheral segment (FIG. 4B) or intact SLNs (FIG. 4C). In addition to continuous 40 Hz stimulation, intermittent (1 s-on and 8 s-off, and also 1 s-on and 4 s-off) 40 Hz stimulation of the intact SLNs was tested in 5 rats. Such burst stimulation also produced an increase in iCT secretion similarly to the continuous 40 Hz stimulation (FIG. 4C).

The systemic arterial blood pressure was not influenced by stimulation of cut CSTs or cut SLNs, but was significantly increased by stimulation of intact SLNs. Mean increase during stimulation was 11 mmHg 14 mmHg and 7 mmHg (12%, 19%, and 11% of prestimulus levels) at 10, 20, and 40 Hz, respectively. Plasma flow significantly decreased by 7±2, 10±4, and 8±4 μl/min during 5, 20 and 40 Hz of cut CST stimulation, and increased by 7±2, 12±5, and 15±4 μl/min during 5, 20 and 40 Hz of cut SLN stimulation, respectively. The frequency-dependent flow increase during SLN stimulation was also observed by intact SLN stimulation by 7±2, 10±2, and 13±2 μl/min during stimulation at 10, 20 and 40 Hz. The frequency dependent decrease in iCT secretion during CST stimulation was in parallel with the decrease in thyroid plasma flow. However, selective increase in iCT during SLN stimulation at 40 Hz was in contrast to the gradual increases in the plasma flow response at 5-40 Hz in response to cut SLNs or intact SLNs.

iPTH Secretion

Basal secretion rates of iPTH were not significantly different between CST or SLN cut and intact conditions (Table 2).

In contrast that iCT secretion decreased during CST stimulation, iPTH secretion increased during the CST stimulation. iPTH secretion was not affected by CST stimulation at 2 Hz, but tended to increase by stimulation at higher frequencies. Significant increase (p<0.05) was observed at 20 Hz (FIG. 5A). The level of iPTH secretion was increased during stimulation, and was returned to prestimulus control level after the end of stimulation. The increased secretion reached twice as high as the prestimulus control level. iPTH secretion was not significantly affected by SLN stimulation at any frequencies irrespective of cut or intact nerve (FIG. 5B, C).

iT3 and iT4 Secretion

There were no significant differences between CST or SLN cut and intact conditions in basal secretion of either iT3 or iT4 (Table 2). iT4 secretion decreased during CST stimulation, but increased during SLN stimulation. Changes in iT3 secretion were similar to those in iT4.

Electrical stimulation of CSTs did not produce any significant changes in iT3 or iT4 at 2 Hz. CST stimulation tended to decrease iT4 secretion at 5-40 Hz. A significant decrease was observed in iT4 following CST stimulation at 20 Hz (FIG. 6A).

Electrical stimulation of cut SLNs did not produce significant changes in iT3 or iT4 at 2 Hz, but significantly increased at higher frequencies (FIG. 6B), being consistent with previous study of radiolabelled iodide output measured in thyroid vein in dogs (Ishii et al., 1968). Intact SLN stimulation also produced increases in both iT3 and iT4 secretion significantly at 20 Hz and 40 Hz (FIG. 6C). In addition to continuous 40 Hz stimulation, intermittent (1 s-on and 8 s-off, and also is on and 4 s off) 40 Hz stimulation of the intact SLNs was tested in 5 rats. Such burst stimulation also produced an increase in iT3 and iT4 secretion similarly to the continuous 40 Hz stimulation (FIG. 6C). Whilst SLN stimulation resulted in concomitant changes in iT3 and iT4 secretion, it is expected that this will be outweighed by the larger increases in iCT secretion observed following SLN stimulation.

Additional Analysis

To further confirm the results above, the secretion rates were re-calculated using a different equation:

$$\text{Secretion rate} = \text{concentration in thyroid venous plasma} \times \text{thyroid venous plasma flow rate}$$

Using the re-calculated values, the data of Experiment 1 were re-analyzed using the same methods as described above, and plotted as shown in FIGS. 7-10 (corresponding to FIGS. 3-6, respectively). As can be seen, while the values in FIGS. 7-10 differ slightly from those of FIGS. 3-6, the conclusions and trends remain the same.

Example 2

Effect of SLN Stimulation in Conscious Rats on Calcitonin Secretion

In order to evaluate the effect of SLN stimulation on calcitonin (CT) level in conscious animals, Sprague-Dawley male and female rats (weight range 360-405 g) were first surgically prepared for conscious SLN stimulation and blood withdrawal. Anesthesia was induced with Isoflurane (1-4% inhalation). Antibiotics and analgesics were administered (carprofen 5 mg/kg subcutaneous; cefazolin 50 mg/Kg subcutaneous; buprenorphine 0.03 mg/kg subcutaneous). The surgical area was trimmed and sterilized (iodine solution and 70% isopropyl ethanol) and ophthalmic ointment applied to the eyes. Procaine hydrochloride was given subcutaneously, and an incision made in the ventral neck to isolate the jugular vein, which was catheterised (polyurethane tubing outer diameter 1.02 mm/inner diameter 0.62 mm) and secured with sterilized suture. The catheter was guided from the ventral neck to the back under the skin using a trocar and fixed to the skin with sterilized suture and tissue adhesive bond (Vet Bond). Procaine hydrochloride was applied to the scalp, with incision and electrode socket fixed on the skull with screws and dental cement. The electrode leads for electrical stimulation were guided from the dorsal head to the ventral neck under the skin using a trocar. Stimulation electrodes were fixed on the SLN at the front neck (CorTec, diameter 200 μm), being placed 8 mm central from the thyroid gland. These electrode cuffs were fixed with the nerves using tissue adhesives (TISSEL). The skin was sutured, anesthesia stopped, and the rats maintained on heat pad during recovery from anesthesia. Antibiotic (cefazolin) was subcutaneously administered for consecutive 2 days after the surgery, and analgesic (buprenorphine) and analgesic anti-inflammatory agent (carprofen) provided for 5 consecutive days after the surgery. The heparin-glucose lock solution in the jugular catheter was replaced every 3-4 days.

When the rats had recovered from surgery (e.g. body weight recovery to the pre-operative levels), they progressed to be assessed for SLN stimulation in the conscious setting. In order to do so, sampling of blood from the jugular vein to measure CT levels was done in parallel to the SLN stimulation, as was done for the assessment described in Example 1 for anesthetized animals.

For the neuromodulation and SLN stimulation, rats were exposed to low dosage of anesthetics (1.5% isoflurane), in order to allow a stress-free connection of the jugular catheter and the electrode stimulation cable. This was followed by 60 minutes acclimatization and recovery.

During the experiment, seven blood samples were collected from each of the four rats and the CT level was measured. The stimulation and blood collection schedule was as follows:
  A baseline blood sample (0.5 mL) was collected from the jugular catheter over 6 minutes (Sample 1).
  At the 18th minute the first SLN stimulation was initiated (Stimulation 1).
  At the 20th minute a blood sample (0.5 mL) was collected from the jugular catheter over 6 minutes (Sample 2).
  Rats recovered for 34 minutes, followed by a blood sample collection (0.5 mL) at the 60th minute, over 6 minutes (Sample 3).
  At the 78th minute a second SLN stimulation was initiated (Stimulation 2).
  At the 80th minute, a blood sample (0.5 mL) was collected over 6 minutes (Sample 4).
  Rats recovered for 34 minutes, with a blood sample collection (0.5 mL) at 120 minutes, over 6 minutes (Sample 5).
  At the 138th minute a third SLN stimulation was initiated (Stimulation 3).
  At the 140th minute, a blood sample (0.5 mL) was collected over 6 minutes (Sample 6).
  Rats then finally recovered for 34 minutes before a final blood collection (0.5 mL) at 180 minutes, over 6 minutes (Sample 7).
Stimulation in this experiment was applied with rectangular pulses by an electric stimulator (SEN-7203; Nihon Kohden) and stimulus isolation unit (SS-202J; Nihon Kohden). The stimulation patterns that were assessed are:
  Continuous stimulation: 6 minutes, 90 μA, 40 Hz;
  Intermittent stimulation (also referred to as Intermittent 1-4): 6 minutes of 1 second on/4 seconds off, 90 μA, 40 Hz; or
  Intermittent stimulation (also referred to as Intermittent 1-8): 6 minutes of 1 second on/8 seconds off, 90 μA, 40 Hz.

The experiment was conducted on four rats, each receiving three trials of stimulation:
  Rat A—Received bilateral SLN stimulation. Trial 1=Continuous, Trial 2=
  Intermittent 1-4, 3=Intermittent 1-8.
  Rat B—Received unilateral SLN stimulation (right side). Trial 1=Intermittent 1-4, Trial 2=Continuous, Trial 3=Intermittent 1-8.
  Rat C—Received unilateral SLN stimulation (right side). Trial 1=Continuous, Trial 2=Intermittent 1-4, Trial 3=Intermittent 1-8.
  Rat D—Rat C—Received unilateral SLN stimulation (left side). Trial 1=Continuous, Trial 2=Intermittent 1-4, Trial 3=Intermittent 1-8.
Results Rat A underwent bilateral SLN simulation, where the basal systemic levels of CT were 7.3 pg/mL. Following continuous stimulation, these levels increased to 15.8 pg/mL. In addition, when intermittent stimulation was administered over 6 minutes with a stimulation cycle of 1 second on/4 seconds off, and 1 second on/8 seconds off, the levels of CT in the conscious animal gradually increased (FIG. 11A).

Figure 11:
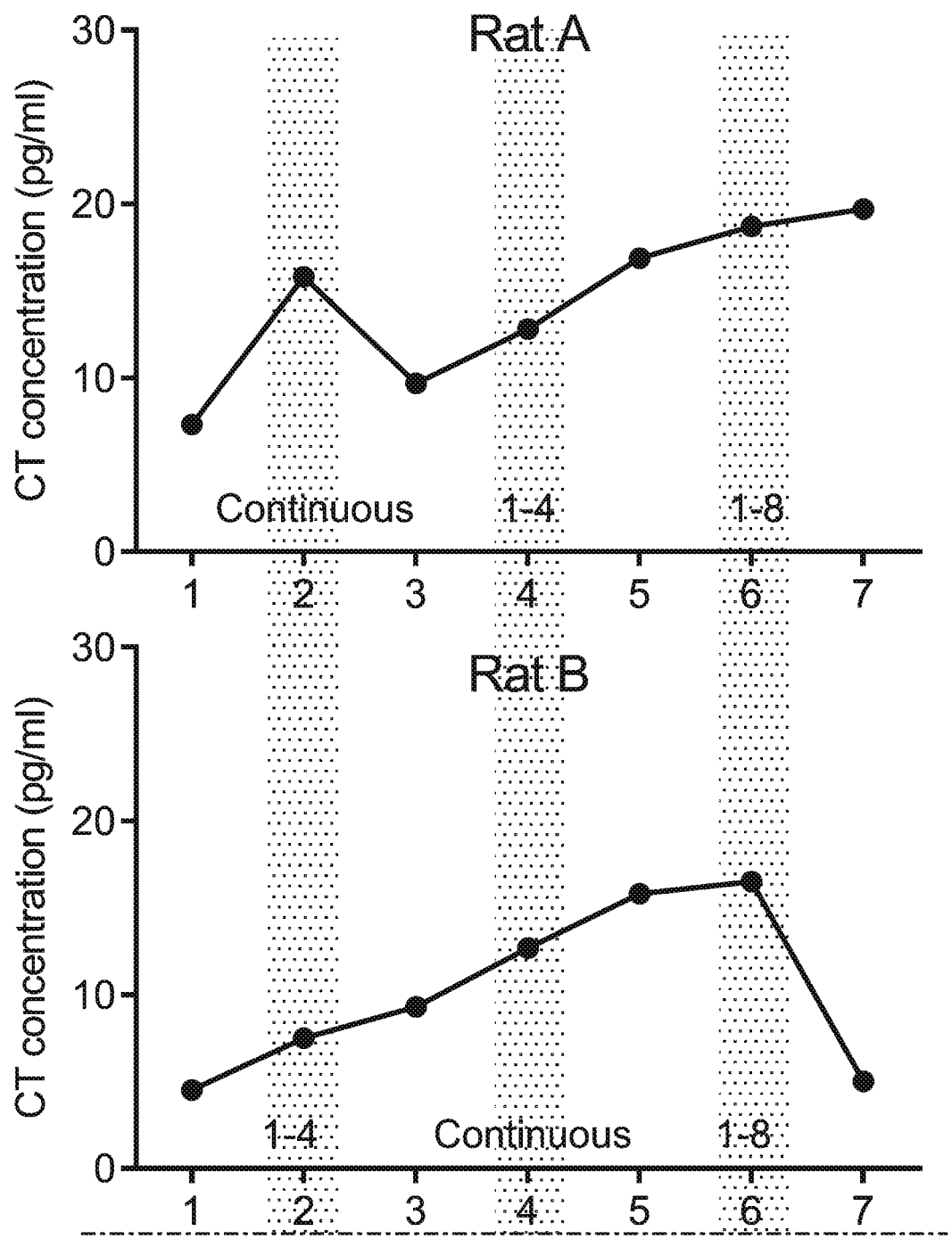
FIG. 11: Changes in systemic plasma iCT concentration in conscious rats following continuous or intermittent stimulation of SNL bilaterally (rat A) or unilaterally (rats B, C, D). "Continuous"—continuous stimulation; "1-4"—intermittent stimulation 1 second on/4 seconds off; "1-8"—intermittent stimulation 1 second on/8 seconds off.

In Rats B, C, and D, in which the SLN was stimulated unilaterally, there was an overall increase in the systemic CT levels with the differing stimulation paradigms, i.e. continuous, and intermittent (1 second on/4 seconds off, or 1 second on/8 seconds off) (FIG. 11B-D).

The invention claimed is:
1. A method of treating a disease in a subject comprising implanting in said subject an apparatus or system for stimulating the neural activity of superior laryngeal nerve (SLN) in the subject, said apparatus or system comprising at least one actuator configured to apply a signal to the SLN of the subject and a controller coupled to the at least one actuator, the controller controlling the signal to be applied by the at least one actuator, wherein the signal stimulates the neural activity of the SLN to produce a physiological response in the subject;
  i) positioning the at least one actuator of the apparatus in signaling contact with the SLN of the subject; and
  ii) activating the apparatus or system, wherein said physiological response is selected from the group consisting of: an increase in circulating calcitonin, an increase in bone density, a decrease in bone resorption, an increase in bone formation and a combination thereof and,
  wherein the signal has a signal intensity of 0.1 T-5.0 T.
2. An apparatus for stimulating the neural activity of superior laryngeal nerve (SLN) of a patient, the apparatus comprising:
  an actuator configured to apply a signal to the SLN of the patient; and
  a controller coupled to the actuator, the controller controlling the signal to be applied by the actuator, wherein the signal stimulates the neural activity of the SLN to produce a physiological response in the patient, wherein said physiological response is selected from the group consisting of: an increase in circulating calcitonin, an increase in bone density, a decrease in bone resorption, an increase in bone formation and a combination thereof and wherein the signal has a signal intensity of 0.1 T-5.0 T.

3. The apparatus according to claim 2, wherein the signal is selected from the group consisting of an electrical signal, an optical signal, an ultrasonic signal and a thermal signal.

4. The apparatus according to claim 2, wherein the signal is an electrical signal, and the actuator configured to apply said electrical signal is an electrode.

5. The apparatus according to claim 4, wherein said electrode is a cuff electrode.

6. The apparatus according to claim 2, wherein the signal comprises an alternating current (AC) waveform or a direct current (DC) waveform.

7. The apparatus according to claim 2, wherein the signal comprises an electrical signal having a frequency of 0.1-100 Hz.

8. The apparatus according to claim 2, wherein the signal has an current of 500 µA or less.

9. The apparatus according to claim 2, wherein the signal is an electrical signal having a pulse width of 0.01 ms-1 ms.

10. The apparatus according to claim 2, wherein the actuator applies the signal intermittently.

11. The apparatus according to claim 2, wherein the actuator applies the signal continuously.

12. The apparatus according to claim 2, wherein the apparatus further comprises a detector element to detect one or more physiological parameters in the patient.

13. The apparatus according to claim 12, wherein the controller is coupled to said detector element, and causes the signal to be applied when the physiological parameter is detected to be meeting or exceeding a predefined threshold value.

14. The apparatus according to claim 13, wherein one or more of the detected physiological parameters is selected from the group consisting of sympathetic tone, parasympathetic tone, circulating calcitonin, circulating T4, circulating T3, or circulating PTH.

15. The apparatus according to claim 13, wherein the one or more detected physiological parameters comprise an action potential or pattern of action potentials in a nerve of the patient, wherein the action potential or pattern of action potentials is associated with a calcitonin-associated disease.

16. The apparatus according to claim 13, wherein the one or more detected physiological parameters comprise an action potential or pattern of action potentials in a nerve of the patient, wherein the action potential or pattern of action potentials is associated with a thyroxine-associated disease.

17. The apparatus according to claim 15, wherein the action potential or pattern of action potentials is in a SLN.

18. The apparatus according to claim 2, wherein application of the signal increases neural activity in at least part of the SLN.

19. The apparatus according to claim 2, wherein the stimulation of neural activity as a result of the actuator applying the signal is substantially persistent.

20. The apparatus according to claim 2 wherein the apparatus is suitable for at least partial implantation into the patient.

21. A method of treating a calcitonin-associated disease in a patient comprising applying a neuromodulatory electrical waveform to a SLN of the patient, wherein the waveform has a frequency of 10-50 Hz and intensity of 0.5 T-5.0 T wherein when applied to a SLN of the patient, the waveform increases neural signaling in the SLN to which the signal is applied, wherein the signal stimulates the neural activity of the SLN to produce a physiological response in the patient, wherein said physiological response is selected from the group consisting of: an increase in circulating calcitonin, an increase in bone density, a decrease in bone resorption, an increase in bone formation and a combination thereof.

* * * * *